(12) United States Patent
Marr et al.

(10) Patent No.: US 10,899,919 B2
(45) Date of Patent: *Jan. 26, 2021

(54) 4- AND 5-SUBSTITUTED 1,2,3-TRIAZOLE, AND REGIOISOMER MIXTURES THEREOF, MODIFIED POLYMERS

(71) Applicant: ISP INVESTMENTS LLC, Wilmington, DE (US)

(72) Inventors: Brian B. Marr, Hampton, NJ (US); Osama M. Musa, Kinnelon, NJ (US)

(73) Assignee: ISP INVESTMENTS LLC, Wilmington, DE (US)

( * ) Notice: Subject to any disclaimer, the term of this patent is extended or adjusted under 35 U.S.C. 154(b) by 76 days.

This patent is subject to a terminal disclaimer.

(21) Appl. No.: 15/018,221

(22) Filed: Feb. 8, 2016

(65) Prior Publication Data

US 2016/0152814 A1 Jun. 2, 2016

Related U.S. Application Data

(62) Division of application No. 14/126,282, filed as application No. PCT/US2012/042702 on Jun. 15, 2012, now Pat. No. 9,334,351.

(Continued)

(51) Int. Cl.
*C08F 220/08* (2006.01)
*C08L 33/00* (2006.01)
(Continued)

(52) U.S. Cl.
CPC ............ *C08L 33/00* (2013.01); *A61K 8/8141* (2013.01); *A61K 47/32* (2013.01); *A61Q 19/00* (2013.01);
(Continued)

(58) Field of Classification Search
CPC ........... C08F 8/00; C08F 8/30; C08F 220/08; C07D 403/12; A61K 47/32; A61K 8/8141;
(Continued)

(56) References Cited

U.S. PATENT DOCUMENTS 5,160,349 A 11/1992 Cardis et al.
6,646,082 B2 11/2003 Ghosh et al.
(Continued)

FOREIGN PATENT DOCUMENTS

WO WO2006115547 A2 11/2006
WO WO2010104837 A1 2/2009
WO WO2010/044752 A1 4/2010

OTHER PUBLICATIONS https://en.oxforddictionaries.com/definition/sun Apr. 15, 2017.*
https://en.oxforddictionaries.com/definition/oilfield Apr. 15, 2017.*
(Continued)

*Primary Examiner* — Irina S Zemel
*Assistant Examiner* — Jeffrey S Lenihan
(74) *Attorney, Agent, or Firm* — William J. Davis; Nathalie Tietcheu

(57) ABSTRACT

Provided are novel 4- and 5-substituted 1,2,3-triazoles, and regioisomer mixtures thereof, modified polymers, wherein the substituted 1,2,3-triazoles are modified by reaction with a modifying polymer (maleic anhydride based polymer). Depending upon the ratio of the substituted 1,2,3-triazole to the maleic anhydride based polymer employed, the resulting modified polymers can provide maleic anhydride based polymers that are partially or fully reacted with the substituted 1,2,3-triazoles. The resulting modified polymers may be partially or fully opened to provide amic acids, carboxylic acids, carboxylic acidic salts, imides, or esters. The novel 4- or 5-substituted 1,2,3-triazoles, and regioisomer mixtures thereof, modified polymers can be converted to a wide variety of useful polymers and may be employed in a wide variety of compositions. An example of a modified polymer may be represented by the structure: formula: (1) wherein m, n, and q are defined herein.

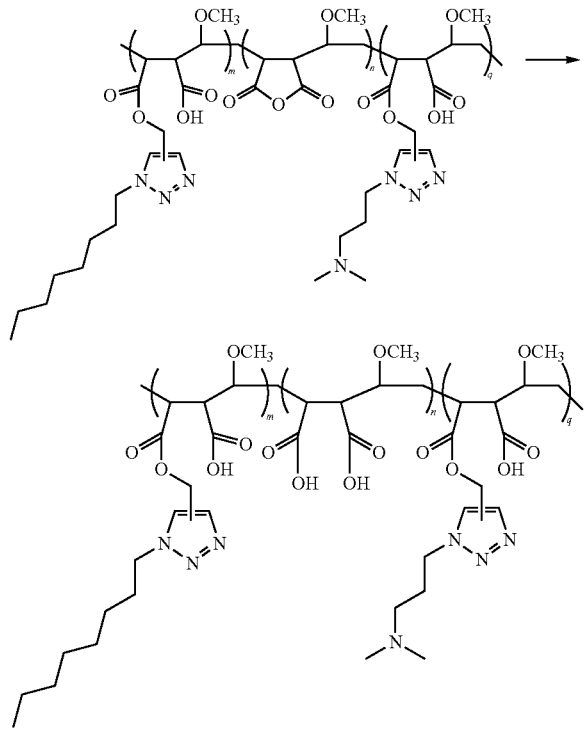

11 Claims, No Drawings

Related U.S. Application Data

(60) Provisional application No. 61/498,233, filed on Jun. 17, 2011.

(51) Int. Cl.
 *C07D 403/12* (2006.01)
 *A61K 8/81* (2006.01)
 *A61K 47/32* (2006.01)
 *A61Q 19/00* (2006.01)
 *C11D 3/37* (2006.01)

(52) U.S. Cl.
 CPC .......... *C07D 403/12* (2013.01); *C08F 220/08* (2013.01); *C11D 3/3757* (2013.01); *C08L 2203/02* (2013.01)

(58) Field of Classification Search
 CPC ..... A61Q 19/00; C08L 33/00; C08L 2203/02; C11D 3/3757
 See application file for complete search history.

(56) References Cited

U.S. PATENT DOCUMENTS

| | | |
|---|---|---|
| 7,311,856 B2 | 12/2007 | Zhou et al. |
| 7,985,424 B2 | 7/2011 | Tomalia et al. |
| 9,334,351 B2* | 5/2016 | Marr .................... C07D 403/12 |
| 2002/0022700 A1 | 2/2002 | Chino et al. |
| 2003/0063998 A1 | 4/2003 | Ghosh et al. |
| 2003/0063999 A1 | 4/2003 | Ghosh et al. |
| 2007/0298006 A1 | 12/2007 | Tomalia et al. |
| 2008/0103236 A1 | 5/2008 | Stokes et al. |
| 2009/0047517 A1 | 2/2009 | Caruso et al. |

OTHER PUBLICATIONS

International Search Report, PCT/US2012/042702 dated Jun. 15, 2012.

Definition of "oilfield" available at http://www.merriam-webster.com/dictionary/oil%20field on Nov. 16, 2015.

* cited by examiner

4- AND 5-SUBSTITUTED 1,2,3-TRIAZOLE, AND REGIOISOMER MIXTURES THEREOF, MODIFIED POLYMERS

BACKGROUND OF THE INVENTION

Field of the Invention

Provided are novel 4- and 5-substituted 1,2,3-triazoles, and regioisomer mixtures thereof, modified polymers, wherein the substituted 1,2,3-triazoles are modified by reaction with a modifying polymer (maleic anhydride based polymer). Depending upon the ratio of the substituted 1,2,3-triazole to the maleic anhydride based polymer employed, the resulting modified polymers can provide maleic anhydride based polymers that are partially or fully reacted with the substituted 1,2,3-triazoles. The resulting modified polymers may be partially or fully opened to provide amic acids, carboxylic acids, carboxylic acidic salts, imides, esters, and mixtures thereof. The mixtures of 4- and 5-substituted regioisomers of 1,2,3-triazoles may be used as mixtures or may be separated to provide purified modified polymers. The novel 4- or 5-substituted 1,2,3-triazoles, and regioisomer mixtures thereof, modified polymers can be converted to a wide variety of useful polymers. The novel modified polymers of the invention can be employed in a wide variety of compositions.

Description of Related Art

Reactions of maleic anhydride based polymers with amines and alcohols to provide polymeric imides, amic acids, and maleic anhydride half esters and full esters are known, U.S. Pat. No. 6,025,501. These polymeric products are particularly useful in pharmaceutical compositions and personal care compositions, such as hair care and skin care products.

Modification of 4- and 5-substituted 1,2,3-triazoles, and regioisomer mixtures thereof, to provide modified polymers that result in a difference in the physical or mechanical properties of the polymers could provide additional useful personal care and pharmaceutical products. The resulting modification of the physical or mechanical properties would depend upon the type of the modifying polymer and the 4- and 5-substituted 1,2,3-triazole employed.

Accordingly, there is a need for polymers resulting from modification of 4- and 5-substituted 1,2,3-triazoles, and regioisomer mixtures thereof, with modifying maleic anhydride based polymers to alter or improve the physical and mechanical properties of such polymers.

SUMMARY OF THE INVENTION

The invention provides 4- and 5-substituted 1,2,3-triazole, or regioisomer mixtures thereof, modified polymers, wherein the substituted 1,2,3-triazole is modified by a modifying polymer represented by the structure:

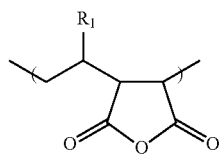

wherein $R_1$ is selected from the group consisting of hydrogen, functionalized and unfunctionalized alkyl, alkoxy, cycloalkyl, alkenyl, and aryl groups, wherein any of the before mentioned groups may be with or without heteroatoms, and mixtures thereof.

Examples of modified polymers may be represented by the structures:

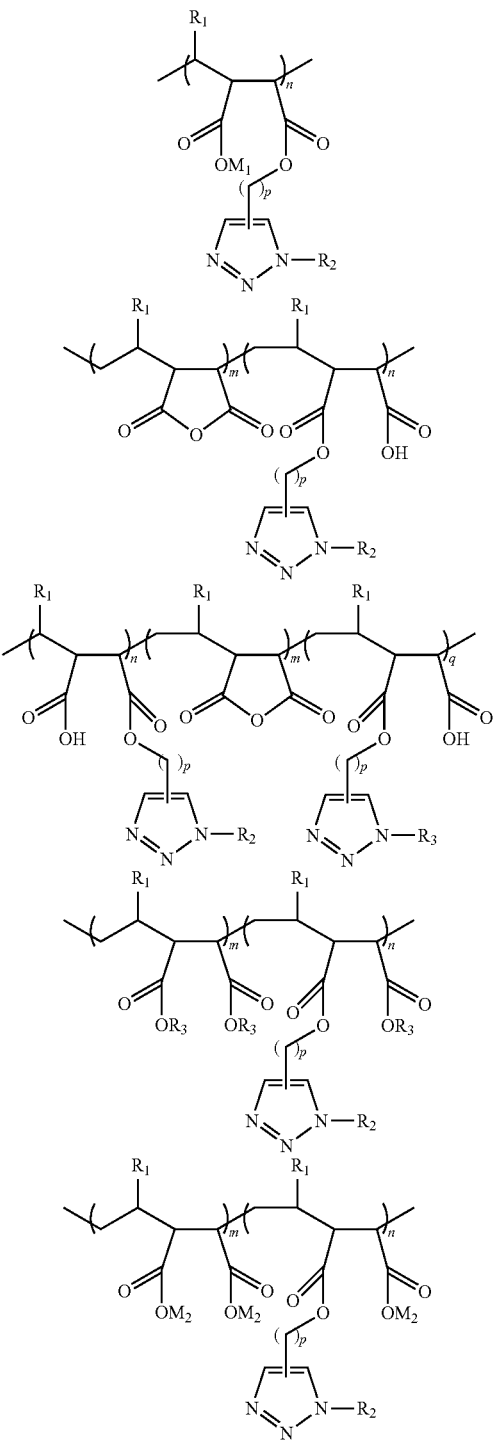

wherein $R_1$, $R_2$, and $R_3$ are each independently selected from the group consisting of hydrogen, functionalized and unfunctionalized alkyl, alkoxy, cycloalkyl, alkenyl, and aryl groups, wherein any of the before mentioned groups may be with or without heteroatoms, and mixtures thereof; $M_1$ is selected from the group consisting of hydrogen, alkali metals, and alkaline earth metals; $M_2$ is an alkali metal or an alkaline earth metal; each m, n, and q is an integer independently ranging from about 2 to about 500; and each p is an integer independently ranging from 1 to about 50.

DETAILED DESCRIPTION

In one aspect, novel 4- and 5-substituted 1,2,3-triazoles, and regioisomer mixtures thereof, modified polymers are provided. The substituted 1,2,3-triazoles are modified by reaction with a modifying polymer, such as a maleic anhydride based polymer. Depending upon the ratio of the maleic anhydride based polymer to the substituted 1,2,3-triazole employed, the resulting modified polymers can provide maleic anhydride based polymers that are partially or fully reacted with the substituted 1,2,3-triazoles. The resulting modified polymers may be partially or fully ring-opened to provide amic acids, carboxylic acids, carboxylic acidic salts, imides, esters, and mixtures thereof. The mixtures of 4- and 5-substituted regioisomers of 1,2,3-triazoles may be used as mixtures or may be separated to provide purified modified polymers. The novel 4- and 5-substituted 1,2,3-triazoles, and regioisomer mixtures thereof, modified polymers can be converted to a wide variety of useful polymers. The polymers may be random, blocked, or alternating polymers.

In another aspect, a wide variety of compositions comprising the novel modified polymers are provided, including adhesives, aerosols, agricultural compositions, beverages, biocides, cleaning compositions, coating compositions, cosmetic compositions, dental compositions, detergents, drugs, electronics, encapsulations, foods, hair sprays, household-industrial-institutional (HI&I), inks, lithographic solutions, membrane compositions, metal fluids, oilfield compositions, paints, paper, personal care compositions, pharmaceuticals, plasters, plastics, printing, and wood-care compositions.

Personal care compositions refers to such illustrative non-limiting compositions as cosmetics, drug delivery systems, hair, oil, pharmaceuticals, pigment dispersions, preservative compositions, including those to alter the color and appearance of the skin, skin, sun, and tissue regeneration scaffolds. Other personal care compositions include, but are not limited to, modified natural oils for increased flexibility in styling, durable styling, increased humidity resistance for hair, skin, and color cosmetics, sun care water-proof/resistance, wear-resistance, shower gels, shampoos, and thermal protecting/enhancing compositions. Dental personal care compositions include denture adhesives, toothpastes, mouth washes, and the like. Pharmaceutical compositions include tablet coatings, tablet binders, transdermal patches, and the like. The wide variety of compositions are described below in detail.

In another embodiment, the invention provides 4- and 5-substituted 1,2,3-triazoles, and regioisomer mixtures thereof, modified polymers having a wide variety of physical and mechanical properties to suit a particular application. The properties of the modified polymers can be designed by selecting the particular type of maleic anhydride based polymer and substituted 1,2,3-triazole employed, and by adjusting the ratio of the maleic anhydride based polymer to the substituted 1,2,3-triazole to partially or fully react the substituted 1,2,3-triazole with the maleic anhydride based polymer. The properties of the modified polymers can be further designed by selecting the degree and type of ring opening of the maleic anhydride based polymer to partially or fully react the maleic anhydride based polymer to provide amic acids, carboxylic acids, carboxylic acidic salts, imides, or esters. Appropriate selection of the types of polymers employed, the ratios of the polymers and the degree and type of ring opening, can be used to provide the desired physical properties of the modified polymer including the hydrophilic, hydrophobic, and mechanical properties.

As used herein, the following terms have the meanings set out below.

The term "amic acid" refers to an organic compound that has both a carboxylic acid and an amide functional group. The nitrogen atom in the amide functional group may or may not be substituted with an organic functional group. Amic acids are also called carbamoyl carboxylic acids.

The term "are each independently selected from the group consisting of" means that when a group appears more than once in a structure, that group may be independently selected each time it appears. For example, in the structure below:

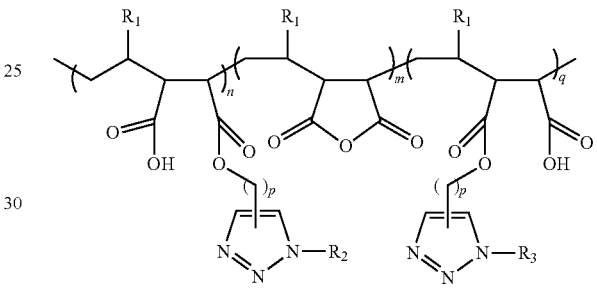

$R_1$ and p each appear more than once. The term "are each independently selected from the group consisting of" means that each $R_1$ and p group may be the same or different.

The symbol of a "bond to the middle of a vinyl group" means that the bond can be attached to either side of the vinyl group and generally means that the structure is referring to a mixture of isomers. For example, in the structure below:

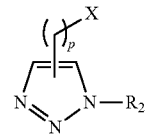

the vinyl group in the triazole moiety containing the

group can be attached to either the 4 or the 5 position of the 1,2,3-triazole moiety. $R_2$, X, and p are defined below.

The term "branched and unbranched alkyl groups" refers to alkyl groups, which may be straight chained or branched. For example, the alkyl groups have from 1 to about 18 carbon atoms, more particularly, from 1 to about 10 carbon atoms, and yet more particularly from 1 to about 6 carbon atoms. Branched groups include isopropyl, tert-butyl, and the like.

The term "copolymer" refers to chains comprising more than one type of monomer unit.

The term "generic substituent(s)" refer(s) to substituent(s) such as $R_1$, $R_2$, $R_3$, $M_1$, $M_2$, m, n, and p, used and defined in the present invention.

The term "halogen" refers to chloro, bromo, iodo and fluoro, and in one embodiment is bromo and/or chloro.

The term "heteroatom" refers to atoms such as oxygen, nitrogen, sulfur, and phosphorous. When the heteroatom is a nitrogen atom, the nitrogen atom may be present in the form of a quaternary amine.

The term "imide" refers to an organic compound comprising two carbonyl groups (acyl groups) bound to nitrogen atom. The nitrogen atom in the imide functional group may or may not be substituted with an organic functional group.

The term "inert solvent" refers to a solvent that does not interfere chemically with the reaction.

The term "$M_1$" refers to hydrogen or an alkali metal or an alkaline earth metal. The alkali metals comprise lithium, sodium, potassium, rubidium, caesium, and francium; in one embodiment, the alkali metal is lithium, sodium, or potassium. The alkaline earth metals comprise beryllium, magnesium, calcium, strontium, barium, and radium, in one embodiment, the alkaline earth metal is magnesium or calcium.

The term "$M_2$" refers to an alkali metal or an alkaline earth metal. The alkali metals comprise lithium, sodium, potassium, rubidium, caesium, and francium; in one embodiment the alkali metal is lithium, sodium, or potassium. The alkaline earth metals comprise beryllium, magnesium, calcium, strontium, barium, and radium, in one embodiment the alkaline earth metal is magnesium or calcium.

The term "modifying polymer" refers to a maleic anhydride based polymer represented by the structure:

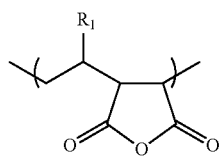

wherein $R_1$ is defined herein.

The term "modified polymer" refers to a 4- or 5-substituted 1,2,3-triazole, or regioisomer mixtures thereof, modified by a modifying polymer, as defined above. Illustrative non-limiting examples of modified polymers are set out above in the Summary of the Invention.

The term "monomer" refers to the repeat units comprising a polymer. A monomer is a small molecule that chemically bonds to other monomers to form a polymer.

The term "non-homopolymer" refers to a polymer formed from two or more monomers and includes essentially all polymers that are not homopolymers. Nonlimiting examples of non-homopolymers include copolymers, terpolymers, tetramers, and the like, wherein the non-homopolymer is a random, blocked, or alternating polymer.

The term "polymer" refers to a large molecule (macromolecule) composed of repeating structural units (monomers) connected by covalent chemical bonds.

The term "polymerization" refers to methods for chemically reacting monomer compounds to form polymer chains. The polymer chain may be alternating, blocked, or random. The type of polymerization method may be selected from a wide variety of methods. Such methods include, but are not limited to, free radical polymerization methods, such as classical radical polymerization and controlled radical polymerization, Nitroxide Mediation Polymerization (NMP), Atom Transfer Radical Polymerization (ATRP), and Reversible Addition Fragmentation Chain-Transfer (RAFT).

The term "respectively" is a term that denotes that the items in a list correspond to each other in the order they are given. With reference to two or more items, the term refers in a parallel or sequential manner.

The term "4- or 5-substituted 1,2,3-triazole, or regioisomer mixtures thereof" refers to 4-substituted 1,2,3-triazoles, 5-substituted 1,2,3-triazoles, and 4- and 5-regioisomer mixtures of substituted 1,2,3-triazoles, respectively. Some non-limiting examples of structures of 4-substituted 1,2,3-triazoles include:

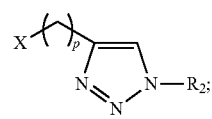

some non-limiting examples of 5-substituted 1,2,3-triazoles include:

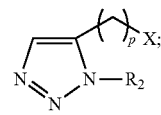

and some non-limiting examples of 4- and 5-regioisomer mixtures of substituted 1,2,3-triazoles include:

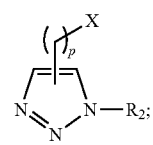

wherein $R_2$, X, and p are defined herein.

As set out above, provided are novel 4- and 5-substituted 1,2,3-triazoles, and regioisomer mixtures thereof, modified polymers. The substituted 1,2,3-triazoles are modified by a modifying polymer, which is a maleic anhydride based polymer represented by the structure:

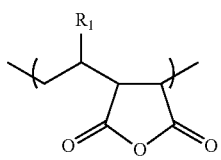

wherein $R_1$ is selected from the group consisting of hydrogen, functionalized and unfunctionalized alkyl, alkoxy, cycloalkyl, alkenyl, and aryl groups, wherein any of the before mentioned groups may be with or without heteroatoms, and mixtures thereof. In one embodiment, $R_1$ is selected from the group consisting of hydrogen and functionalized and unfunctionalized alkyl and alkoxy groups, wherein any of the before mentioned groups may be with or without heteroatoms, and mixtures thereof. More particularly, $R_1$ is selected from the group consisting of functionalized and unfunctionalized alkyl and alkoxy groups.

The 4- and 5-substituted 1,2,3-triazoles, and regioisomer mixtures thereof, are represented by the structures, respectively:

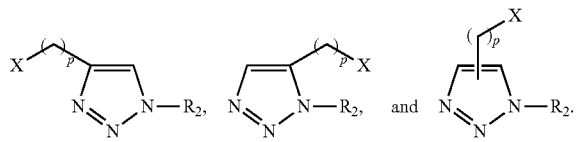

Each X is OH or $NHR_2$. In one embodiment, each X is OH. Each $R_2$ is independently selected from the group consisting of hydrogen, functionalized and unfunctionalized alkyl, alkoxy, cycloalkyl, alkenyl, and aryl groups, wherein any of the before mentioned groups may be with or without heteroatoms, and mixtures thereof. In a separate embodiment, each $R_2$ is independently selected from the group consisting of hydrogen and functionalized and unfunctionalized alkyl and alkoxy groups, wherein any of the before mentioned groups may be with or without heteroatoms, and mixtures thereof. More particularly, each $R_2$ is independently selected from the group consisting of functionalized and unfunctionalized alkyl and alkoxy groups. Each p is an integer independently ranging from 1 to about 50. In another embodiment, each p is an integer independently ranging from 1 to about 15. More particularly, each p is an integer independently ranging from 1 to about 6.

Examples of modified polymers according to the invention may be represented by the structures:

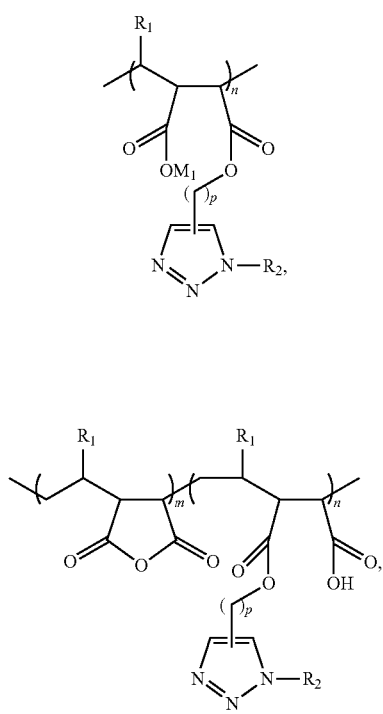

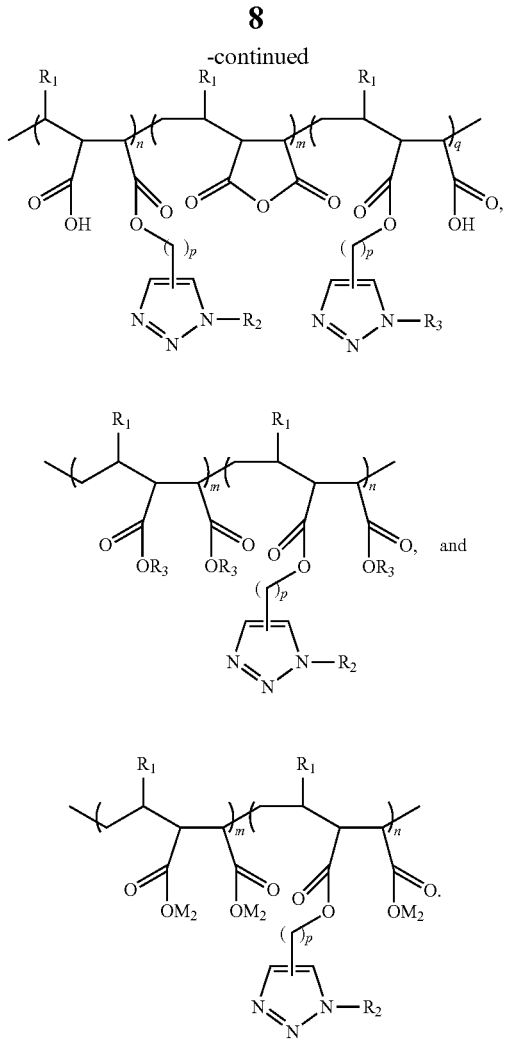

$R_1$, $R_2$, and $R_3$ are each independently selected from the group consisting of hydrogen, functionalized and unfunctionalized alkyl, alkoxy, cycloalkyl, alkenyl, and aryl groups, wherein any of the before mentioned groups may be with or without heteroatoms, and mixtures thereof. For example, in an embodiment, each $R_1$, $R_2$, and $R_3$ is independently selected from the group consisting of hydrogen and functionalized and unfunctionalized alkyl and alkoxy groups, wherein any of the before mentioned groups may be with or without heteroatoms, and mixtures thereof. More particularly, each $R_1$, $R_2$, and $R_3$ is independently selected from the group consisting of functionalized and unfunctionalized alkyl and alkoxy groups. Each $M_1$ is independently selected from the group consisting of hydrogen, alkali metals, and alkaline earth metals. Each $M_2$ is independently an alkali metal or an alkaline earth metal. Each m, n, and q is an integer independently ranging from about 2 to about 500. In one aspect, each m, n, and q is an integer independently ranging from about 2 to about 100. More particularly, each m, n, and q is an integer independently ranging from about 2 to about 50. Each p is an integer independently ranging from 1 to about 50, and particularly, each p is an integer independently ranging from 1 to about 15. More particularly, each p is an integer independently ranging from 1 to about 6.

In one embodiment, the modified polymer is represented by the structure:

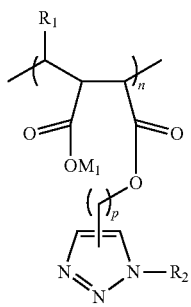

wherein the generic substituents are defined above.

In another embodiment, the modified polymer is represented by the structure:

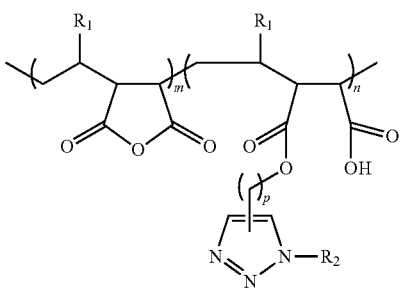

wherein the generic substituents are defined above.

In another embodiment, the modified polymer is represented by the structure:

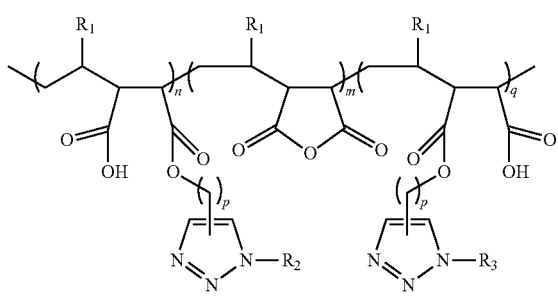

wherein the generic substituents are defined above.

In another embodiment, the modified polymer is represented by the structure:

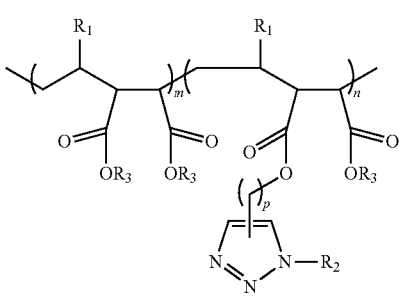

wherein the generic substituents are defined above.

In yet another embodiment, the modified polymer is represented by the structure:

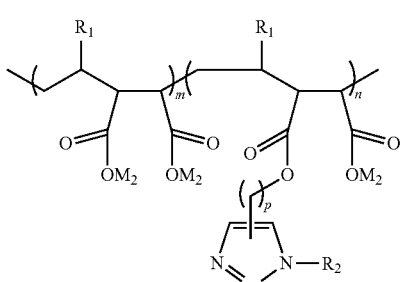

wherein the generic substituents are defined above.

Depending on the end application, one or more fillers may be included in the compositions and may be added for improved rheological properties and/or stress reduction. Examples of suitable nonconductive fillers include alumina, aluminum hydroxide, silica, fused silica, fumed silica, vermiculite, mica, wollastonite, calcium carbonate, titania, sand, glass, barium sulfate, zirconium, carbon black, organic fillers, and halogenated ethylene polymers, such as, tetrafluoroethylene, trifluoroethylene, vinylidene fluoride, vinyl fluoride, vinylidene chloride, and vinyl chloride. Examples of suitable conductive fillers include carbon black, graphite, gold, silver, copper, platinum, palladium, nickel, aluminum, silicon carbide, boron nitride, diamond, and alumina. Combinations of these fillers may be used.

The filler particles may be of any appropriate size, particularly from the nano to micro range. The choice of such size for any particular end use is within the expertise of one skilled in the art. The filler may be present in an amount from about 10% to about 90% by weight of the total composition. More than one filler type may be used in a composition and the fillers may or may not be surface treated. Appropriate filler sizes can be determined by the practitioner, and, in particular, may be within the range from about 20 nm to about 100 μm.

Other materials, such as adhesion promoters (e.g. epoxides, silanes), dyes, pigments, and rheology modifiers may be added as desired for the modification of the final properties. Such materials and the amounts needed are within the expertise of those skilled in the art.

Mixtures of 4- and 5-substituted regioisomers of 1,2,3-triazoles may be used as mixtures or may be separated, e.g., by chromatography, to provide purified 4-substituted regioisomers and 5-substituted regioisomers of the modified polymers. The novel 4- or 5-substituted 1,2,3-triazoles, and regioisomer mixtures thereof, modified polymers can be converted to a wide variety of useful polymers. The polymers may be random, blocked, or alternating polymers. The novel modified polymers of the invention can be employed in a wide variety of compositions.

Chromatography is the collective term for a group of laboratory techniques for the separation of mixtures. The techniques involve passing a mixture dissolved in a mobile phase through a stationary phase, which separates the analyte to be measured from other molecules in the mixture and allows it to be isolated. Preparative chromatography, one particular technique, separates the components of a mixture for further use and is a form of purification. The various forms of chromatography are well known to those of skill in the art.

The most general technique for separating large amounts of material is column chromatography. Column chromatography is a separation technique in which the stationary bed is within a tube. The particles of the solid stationary phase or the support coated with a liquid stationary phase may fill the whole inside volume of the tube (packed column) or be concentrated on or along the inside tube wall leaving an open, unrestricted path for the mobile phase in the middle part of the tube. Differences in rates of movement through the medium are calculated to different retention times of the sample.

Another technique that may be employed is liquid chromatography, which is a separation technique in which the mobile phase is a liquid. Liquid chromatography can be carried out either in a column or a plane. Liquid chromatography that generally utilizes very small packing particles and a relatively high pressure is referred to as high performance liquid chromatography (HPLC). In the HPLC technique, the sample is forced through a column that is packed with irregularly or spherically shaped particles or a porous monolithic layer (stationary phase) by a liquid (mobile phase) at high pressure. HPLC is generally divided into two different sub-classes based on the polarity of the mobile and stationary phases. The technique in which the stationary phase is more polar than the mobile phase is called normal phase liquid chromatography (NPLC) and the opposite is called reversed phase liquid chromatography (RPLC). Reversed-phase chromatography is an elution procedure used in liquid chromatography in which the mobile phase is significantly more polar than the stationary phase. The appropriate method and conditions of chromatography to separate the mixtures of 4- and 5-substituted regioisomers are well known in the art.

Polymers of the invention may be used in a wide variety of compositions such as in adhesives, agricultural, biocides, coatings, electronics, household-industrial-institutional (HI&I), inks, membranes, metal fluids, oilfield, paper, paints, plastics, printing, plasters, and wood-care compositions.

Compositions belonging to the personal care/cosmetic and pharmaceutical arts find utility in altering, delivering an active, enhancing, improving, modifying the appearance, condition, color, health, style of the skin (including face, scalp, and lips), hair, nails, and oral cavity. Many examples and product forms of these compositions are known. These compositions can impart benefits that include, but are not limited to, hair style flexibility, hair style durability, humidity resistance for hair, color and/or color protection, moisturization, wrinkle reduction, protection from ultraviolet radiation, water proofness, water resistance, wear resistance, thermal protection, adhesion, active ingredient delivery, anti-cavity, and/or anti-gingivitis protection. As such, these compositions are sometimes categorized in the following areas: skin care, hair care (both styling and non-styling), sun care, cosmetics (including color cosmetics), antiperspirants, deodorants, oral hygiene, and men's and women's personal hygiene/grooming. In some cases these benefits and care areas overlap with another.

Skin care compositions include those materials used on the body, face, hands, lips, and/or scalp, and are beneficial for many reasons, such as firming, anti-cellulite, moisturizing, nourishing, cleaning, reducing or eliminating the appearance of wrinkles or lentigo, toning, and/or purifying. They also can be used to sanitize.

Consumers can identify many of the compositions that serve the sun care area, for example after-fun, children's, beach, self-tan, sports (i.e., being sweatproof, waterproof, resistant to running, or having added UV absorbers and/or antioxidants), sensitive skin products (i.e., having low irritation to the eyes and/or skin, and/or being free of fragrances and/or dyes), daily wear, leave-on hair creams, lotions, styling products, and hair sprays. Typically, sun care products also comprise one or more UV actives, which are those organic and inorganic materials that scatter, absorb, and/or reflect radiation having a wavelength from about 100 nm to about 400 nm. In one aspect, the sun care product protects against UV-A and/or UV-B radiation. UV-A radiation, from about 320 nm to about 400 nm, has the longest wavelength within the UV spectrum, and consequently is the least energetic. While UV-A rays can induce skin tanning, they are liable to induce adverse changes as well, especially in the case of sensitive skin or of skin, which is continually exposed to solar radiation. In particular UV-A rays cause a loss of skin elasticity and the appearance of wrinkles, leading to premature skin aging. UV-B rays have shorter wavelengths, from about 290 nm to about 320 nm, and their higher energy can cause erythema and skin burns, which may be harmful. Alternatively, sun care products may omit UV actives, and may be regarded as a tanning oil or a tan promoter. Some sun care compositions may promote soothe skin after sun exposure, and/or be formulated for application to the lips, hair, or the area around the eyes. Self-tan compositions, which are products that color skin without requiring full sun exposure, also fit under the sun care umbrella. The many different sun care product formats include may assume a consistency ranging from liquid to semiliquid forms (e.g., milks, creams), to thicker forms like gels, creams, pastes, and even solid- and wax-like forms. Sun care products also may take the form of an aerosol, spray, mist, roll-on, or wipe.

Hair care compositions include shampoos, leave-on and rinse-out conditioners used for conditioning, moisturizing, repairing, hair colors, hair relaxers, and deep conditioners and treatments such as hot oils and waxes, 2-in-1 shampoo/conditioner combination products, 3-in-1 shampoo/conditioner/styling agent. The many types of hair care products can be delivered in an array of formats, including aerosol sprays, pump sprays, gel sprays, mousses, gels, waxes, creams, pomades, spritzes, putties, lacquers, de-frizzing serums, perms, relaxants and colorants.

Color cosmetic compositions include facial make-up, eye makeup, mascaras, lip and nail products. Facial make-up compositions include foundation (liquid, solid, and semisolid)—skin tinted creams, liquid, sticks, mousses used as a base under make-up, rouge, face powder, blusher, highlighters, face bronzers, concealers, and 2-way cake products.

Personal care/cosmetics also include eye make-up, mascaras, eyeliners, eye shadows, eyebrow pencils and eye pencils. Lip products include lipsticks, lip pencils, lip gloss, transparent bases and tinted lip moisturizers as well as multi-function color sticks that can also be used for cheeks and eyes. Nail products include nail varnishes/enamels, nail varnish removers, treatments, home-manicure products such as cuticle softeners and nail strengtheners.

In addition to the skin, hair, and sun care compositions summarized above, the polymers related herein also find application in oral care compositions. Non-limiting examples or oral care compositions include toothpastes (including toothpaste gels), denture adhesives, whiteners, anesthetics, and dental floss and related products. These compositions may take any product format, such as pastes, gels, creams, solutions, dispersions, rinses, flosses, aerosols, powders, and lozenges.

Grooming products for men and women include shaving products and toiletries, which may find use in preparing the skin and/or hair for dry or wet shaving. In addition, these compositions may help to moisturize, cool, and/or soothe skin. A variety of product forms are known, a few of which are foams, gels, creams, sticks, oils, solutions, tonics, balms, aerosols, mists, sprays, and wipes.

The polymer can also be used in other personal care/cosmetic applications, such as an absorbent material in appropriate applications such as diapers, incontinence products, feminine products, and other related products.

The polymers described herein also find application in bath and shower compositions, such as foams, gels, salts, oils, balls, liquids, powders and pearls. Also included are bar soaps, body washes, shower gels, cleansers, gels, oils, foams, scrubs and creams. As a natural extension of this category, these compositions also include liquid soaps and hand sanitizers used for cleaning hands.

The polymer of the invention can be used in combination with one or more additional personal care/cosmetically acceptable additives chosen from, for example, conditioning agents, protecting agents, such as, for example, hydrosoluble, liposoluble and water-insoluble UV filters, antiradical agents, antioxidants, vitamins and pro-vitamins, fixing agents, oxidizing agents, reducing agents, dyes, cleansing agents, anionic, cationic, nonionic and amphoteric surfactants, thickeners, perfumes, pearlizing agents, stabilizers, pH adjusters, filters, preservatives, hydroxy acids, various cationic, anionic and nonionic polymers, cationic and nonionic polyether associative polyurethanes, vegetable oils, mineral oils, synthetic oils, polyols such as glycols and glycerol, silicones, aliphatic alcohols, colorants, bleaching agents, highlighting agents and sequestrants.

For some embodiments, it may be preferred to add one or more preservatives and/or antimicrobial agents, such as, but not limited to, benzoic acid, sorbic acid, dehydroacetic acid, piroctone olamine, DMDM hydantoin, IPBC, triclosan, bronopol, formaldehyde, isothiazolinones, nitrates/nitrites, parabens, phenoxyethanol, potassium sorbate, sodium benzoate, sulphites, and sulphur dioxide. Combinations of preservatives may be used.

In other embodiments it may be desirable to incorporate preservative boosters/solvents, select examples of which include caprylyl glycol, hexylene glycol, pentylene glycol, ethylhexylglycerin, caprylhydroxamic acid, and glyceryl caprylate. Humectants, which include glycerin, butylene glycol, propylene glycol, sorbitol, mannitol, and xylitol may be added. Polysaccharides, such as gum Arabic, may be included as well. It may be desirable to include one or more other ingredients, such as those described in U.S. patent publication 2010/0183532 and WO 2010/105050, which disclosures are incorporated herein by reference.

These additives may be present in the composition according to the invention in proportions that may range from about 0% to about 20% by weight in relation to the total weight of the composition. The precise amount of each additive may be easily determined by an expert in the field according to its nature and its function.

Examples of these co-ingredients and many others can be found in the following references, each of which is herein incorporated in its entirety by reference: "Inventory and common nomenclature of ingredients employed in cosmetic products," *Official Journal of the European Union*, May 4, 2006, pages L 97/1 through L 97/528; and *International Cosmetic Ingredient Dictionary and Handbook*, 13th edition, ISBN: 1882621476, published by The Personal Care Products Council in January 2010.

Any known conditioning agent is useful in the personal care/cosmetic compositions of this invention. Conditioning agents function to improve the cosmetic properties of the hair, particularly softness, thickening, untangling, feel, and static electricity and may be in liquid, semi-solid, or solid form such as oils, waxes, or gums. Similarly, any known skin-altering agent is useful in the compositions of this invention. A few examples of conditioning agents include cationic polymers, cationic surfactants and cationic silicones. Conditioning agents may be chosen from synthesis oils, mineral oils, vegetable oils, fluorinated or perfluorinated oils, natural or synthetic waxes, silicones, cationic polymers, proteins and hydrolyzed proteins, ceramide type compounds, cationic surfactants, fatty amines, fatty acids and their derivatives, as well as mixtures of these different compounds.

The synthesis oils include polyolefins, e.g., poly-α-olefins such as polybutenes, polyisobutenes and polydecenes. The polyolefins can be hydrogenated. The mineral oils suitable for use in the compositions of the invention include hexadecane and oil of paraffin. Suitable animal and vegetable oils include sunflower, corn, soy, avocado, jojoba, squash, raisin seed, sesame seed, walnut oils, fish oils, glycerol tricaprocaprylate, Purcellin oil or liquid jojoba. Suitable natural or synthetic oils include eucalyptus, lavender, vetiver, litsea cubeba, lemon, sandalwood, rosemary, chamomile, savory, nutmeg, cinnamon, hyssop, caraway, orange, geranium, cade, and bergamot. Suitable natural and synthetic waxes include carnauba wax, candelila wax, alfa wax, paraffin wax, ozokerite wax, vegetable waxes such as olive wax, rice wax, hydrogenated jojoba wax, absolute flower waxes such as black currant flower wax, animal waxes such as bees wax, modified bees wax (cerabellina), marine waxes and polyolefin waxes such as polyethylene wax.

The cationic polymers that may be used as a conditioning agent according to the invention are those known to improve the cosmetic properties of hair treated by detergent compositions. The expression "cationic polymer" as used herein, indicates any polymer containing cationic groups and/or ionizable groups in cationic groups. The cationic polymers used generally have a molecular weight the average number of which falls between about 500 and 5,000,000, for example between 1000 and 3,000,000. Cationic polymers may be chosen from among those containing units including primary, secondary, tertiary, and/or quaternary amine groups that may either form part of the main polymer chain or a side chain. Useful cationic polymers include known polyamine, polyaminoamide, and quaternary polyammonium types of polymers, such as:

(1) homopolymers and copolymers derived from acrylic or methacrylic esters or amides. The copolymers can contain one or more units derived from acrylamides, methacrylamides, diacetone acrylamides, acrylamides and methacrylamides, acrylic or methacrylic acids or their esters, vinyllactams such as vinyl pyrrolidone or vinyl caprolactam, and vinyl esters. Specific examples include: copolymers of acrylamide and dimethyl amino ethyl methacrylate quaternized with dimethyl sulfate or with an alkyl halide; copolymers of acrylamide and methacryloyl oxyethyl trimethyl ammonium chloride; the copolymer of acrylamide and methacryloyl oxyethyl trimethyl ammonium methosulfate; copolymers of vinyl pyrrolidone/dialkylaminoalkyl acrylate or methacrylate, optionally quaternized, such as the products sold under the name Gafquat® by International Specialty Products; the dimethyl amino ethyl methacrylate/vinyl caprolactam/vinyl pyrrolidone terpolymers, such as the product sold under the name Gaffix® VC 713 by International Specialty Products; the vinyl pyrrolidone/methacrylamidopropyl dimethyl amine copolymer, marketed under the name Styleze® CC-10 by International Specialty Products; the vinyl pyrrolidone/quaternized dimethyl amino propyl methacrylamide copolymers such as the product sold under the name Gafquat® HS-100 by International Specialty Products; and the vinyl pyrrolidone/dimethylaminopropyl methacrylamide/$C_9$-$C_{24}$ alkyldimethylaminopropyl methacrylic acid quaternized terpolymers described in U.S. Pat. No. 6,207,778 and marketed under the name Styleze® W-20 by International Specialty Products.

(2) derivatives of cellulose ethers containing quaternary ammonium groups, such as hydroxy ethyl cellulose quaternary ammonium that has reacted with an epoxide substituted by a trimethyl ammonium group.

(3) derivatives of cationic cellulose such as cellulose copolymers or derivatives of cellulose grafted with a hydrosoluble quaternary ammonium monomer, as described in U.S. Pat. No. 4,131,576, such as the hydroxy alkyl cellulose, and the hydroxymethyl-, hydroxyethyl- or hydroxypropyl-cellulose grafted with a salt of methacryloyl ethyl trimethyl ammonium, methacrylamidopropyl trimethyl ammonium, or dimethyl diallyl ammonium.

(4) cationic polysaccharides such as described in U.S. Pat. Nos. 3,589,578 and 4,031,307, guar gums containing cationic trialkyl ammonium groups and guar gums modified by a salt, e.g., chloride of 2,3-epoxy propyl trimethyl ammonium.

(5) polymers composed of piperazinyl units and alkylene or hydroxy alkylene divalent radicals with straight or branched chains, possibly interrupted by atoms of oxygen, sulfur, nitrogen, or by aromatic or heterocyclic cycles, as well as the products of the oxidation and/or quaternization of such polymers.

(6) water-soluble polyamino amides prepared by polycondensation of an acid compound with a polyamine. These polyamino amides may be reticulated.

(7) derivatives of polyamino amides resulting from the condensation of polyalkylene polyamines with polycarboxylic acids followed by alkylation by bi-functional agents.

(8) polymers obtained by reaction of a polyalkylene polyamine containing two primary amine groups and at least one secondary amine group with a dioxycarboxylic acid chosen from among diglycolic acid and saturated dicarboxylic aliphatic acids having 3 to 8 atoms of carbon. Such polymers are described in U.S. Pat. Nos. 3,227,615 and 2,961,347.

(9) the cyclopolymers of alkyl dialyl amine or dialkyl diallyl ammonium such as the homopolymer of dimethyl diallyl ammonium chloride and copolymers of diallyl dimethyl ammonium chloride and acrylamide.

(10) quaternary diammonium polymers such as hexadimethrine chloride. Polymers of this type are described particularly in U.S. Pat. Nos. 2,273,780, 2,375,853, 2,388,614, 2,454,547, 3,206,462, 2,261,002, 2,271, 378, 3,874,870, 4,001,432, 3,929,990, 3,966,904, 4,005,193, 4,025,617, 4,025,627, 4,025,653, 4,026, 945, and 4,027,020.

(11) quaternary polyammonium polymers, including, for example, Mirapol® A 15, Mirapol® AD1, Mirapol® AZ1, and Mirapol® 175 products sold by Miranol.

(12) the quaternary polymers of vinyl pyrrolidone and vinyl imidazole such as the products sold under the names Luviquat® FC 905, FC 550, and FC 370 by BASF.

(13) quaternary polyamines.

(14) reticulated polymers known in the art.

Other cationic polymers that may be used within the context of the invention are cationic proteins or hydrolyzed cationic proteins, polyalkyleneimines such as polyethyleneimines, polymers containing vinyl pyridine or vinyl pyridinium units, condensates of polyamines and epichlorhydrins, quaternary polyurethanes, and derivatives of chitin. In one aspect, the cationic polymers may be derivatives of quaternary cellulose ethers, the homopolymers and copolymers of dimethyl diallyl ammonium chloride, quaternary polymers of vinyl pyrrolidone and vinyl imidazole, and mixtures thereof.

The conditioning agent can be any silicone known by those skilled in the art to be useful as a conditioning agent. The silicones suitable for use according to the invention include polyorganosiloxanes that are insoluble in the composition. The silicones may be present in the form of oils, waxes, polymers, or gums. They may be volatile or non-volatile. The silicones can be selected from polyalkyl siloxanes, polyaryl siloxanes, polyalkyl aryl siloxanes, silicone gums and polymers, and polyorgano siloxanes modified by organofunctional groups, and mixtures thereof. Suitable polyalkyl siloxanes include polydimethyl siloxanes with terminal trimethyl silyl groups or terminal dimethyl silanol groups (dimethiconol) and polyalkyl ($C_1$-$C_{20}$) siloxanes. Suitable polyalkyl aryl siloxanes include polydimethyl methyl phenyl siloxanes and polydimethyl diphenyl siloxanes, linear or branched. The silicone gums suitable for use herein include polydiorganosiloxanes including those having a number-average molecular weight between 200, 000 and 1,000,000, used alone or mixed with a solvent. Examples include polymethyl siloxane, polydimethyl siloxane/methyl vinyl siloxane gums, polydimethyl siloxane/diphenyl siloxane, polydimethyl siloxane/phenyl methyl siloxane and polydimethyl siloxane/diphenyl siloxane/methyl vinyl siloxane. Suitable silicone polymers include silicones with a dimethyl/trimethyl siloxane structure and polymers of the trimethyl siloxysilicate type. The organo-modified silicones suitable for use in the invention include silicones such as those previously defined and containing one or more organofunctional groups attached by means of a hydrocarbon radical and grafted siliconated polymers. In one embodiment the silicones are amino functional silicones. The silicones may be used in the form of emulsions, nano-emulsions, or micro-emulsions.

The conditioning agent can be a protein or hydrolyzed cationic or non-cationic protein. Examples of these compounds include hydrolyzed collagens having triethyl ammonium groups, hydrolyzed collagens having trimethyl ammonium and trimethyl stearyl ammonium chloride groups, hydrolyzed animal proteins having trimethyl benzyl ammonium groups (benzyltrimonium hydrolyzed animal protein), hydrolyzed proteins having groups of quaternary ammonium on the polypeptide chain, including at least one $C_1$-$C_{18}$ alkyl. Hydrolyzed proteins include Croquat™ L, in which the quaternary ammonium groups include a $C_{12}$ alkyl group, Croquat™ M, in which the quaternary ammonium groups include $C_{10}$-$C_{18}$ alkyl groups, Croquat™ S in which the quaternary ammonium groups include a $C_{18}$ alkyl group and Crotein Q in which the quaternary ammonium groups include at least one $C_1$-$C_{18}$ alkyl group. These products are sold by Croda. The conditioning agent can comprise quaternized vegetable proteins such as wheat, corn, or soy proteins such as cocodimonium hydrolyzed wheat protein, laurdimonium hydrolyzed wheat protein and steardimonium hydrolyzed wheat protein.

The conditioning agent can be a ceramide type of compound such as a ceramide, a glycoceramide, a pseudoceramide, or a neoceramide. These compounds can be natural or synthetic. Compounds of the ceramide type are, for example, described in Patents pending DE4424530, DE4424533, DE4402929, DE4420736, WO95/23807, WO94/07844, EP-A-0646572, WO95/16665, FR-2 673 179, EP-A-0227994, WO 94/07844, WO 94/24097, and WO 94/10131. Ceramide type compounds useful herein include 2-N-linoleoyl amino-octadecane-1,3-diol, 2-N-oleoyl amino-octadecane-1,3-diol, 2-N-palmitoyl amino-octadecane-1,3-diol, 2-N-stearoyl amino-octadecane-1,3-diol, 2-N-behenoyl amino-octadecane-1,3-diol, 2-N-[2-hydroxypalmitoyl]-amino-octadecane-1,3-diol, 2-N-stearoyl aminooctadecane-1,3,4-triol, N-stearoyl phytosphingosine, 2-N-palmitoyl amino-hexadecane-1,3-diol, bis-(N-hydroxy ethyl N-cetyl) malonamide, N(2-hydroxy ethyl)-N-(3-cetoxyl-2-hydroxy propyl) amide of cetylic acid, N-docosanoyl N-methyl-D-glucamine and mixtures of such compounds.

The conditioning agent can be a cationic surfactant such as a salt of a primary, secondary, or tertiary fatty amine, optionally polyoxyalkylenated, a quaternary ammonium salt, a derivative of imadazoline, or an amine oxide. Suitable examples include mono-, di-, or tri-alkyl quaternary ammonium compounds with a counter-ion such as a chloride, methosulfate, tosylate, etc. including, but not limited to, cetrimonium chloride, dicetyldimonium chloride, behentrimonium methosulfate, and the like. The presence of a quaternary ammonium compound in conjunction with the polymer described above reduces static and enhances combing of hair in the dry state. The polymer also enhances the deposition of the quaternary ammonium compound onto the hair substrate thus enhancing the conditioning effect of hair.

The conditioning agent can be any fatty amine known to be useful as a conditioning agent; e.g. dodecyl, cetyl or stearyl amines, such as stearamidopropyl dimethylamine. The conditioning agent can be a fatty acid or derivatives thereof known to be useful as conditioning agents. Suitable fatty acids include myristic acid, palmitic acid, stearic acid, behenic acid, oleic acid, linoleic acid, and isostearic acid. The derivatives of fatty acids include carboxylic ester acids including mono-, di-, tri- and tetra-carboxylic acids.

The conditioning agent can be a fluorinated or perfluorinated oil. Fluorinated oils include perfluoropolyethers described in EP-A-486135 and the fluorohydrocarbon compounds described in WO 93/11103. The fluoridated oils may also be fluorocarbons such as fluoramines, e.g., perfluorotributylamine, fluoridated hydrocarbons, such as perfluorodecahydronaphthalene, fluoroesters, and fluoroethers. Of course, mixtures of two or more conditioning agents can be used.

The conditioning agent or agents can be present in an amount from about 0.001% to about 20%, particularly from about 0.01% to about 10%, and even more particularly from about 0.1% to about 3% by weight based on the total weight of the final composition. The personal care/cosmetic compositions of the invention can contain one or more protecting agents in combination with the above-described polymer to prevent or limit the degrading effects of natural physical and/or chemical assaults on the keratinous materials.

The protecting agent can be chosen from hydrosoluble, liposoluble and water-insoluble UV filters, antiradical agents, antioxidants, vitamins and pro-vitamins. The above-described cationic polymer enhances the deposition of these materials onto the hair or skin substrate enhancing protection of hair to UV damage. Organic UV filters (systems that filter out UV rays) can be chosen from among hydrosoluble or liposoluble filters, whether siliconated or nonsiliconated, and mineral oxide particles, the surface of which may be treated. Hydrosoluble organic UV filters may be chosen from para-amino benzoic acid and its salts, anthranilic acid and its salts, salicylic acid and its salts, hydroxy cinnamic acid and its salts, sulfonic derivatives of benzothiazoles, benzimidizoles, benzoxazoles and their salts, sulfonic derivatives of benzophenone and their salts, sulfonic derivatives of benzylidene camphor and their salts, derivatives of benzylidene camphor substituted by a quaternary amine and their salts, derivatives of phthalydene-camphosulfonic acids and their salts, sulfonic derivatives of benzotriazole, and mixtures thereof. Hydrophilic polymers, which have light-protective qualities against UV rays, can be used. These include polymers containing benzylidene camphor and/or benzotriazole groups.

Suitable liposoluble organic UV filters include derivatives of para-aminobenzoic acid, such as the esters or amides of para-aminobenzoic acid; derivatives of salicylic acid; derivatives of benzophenone; derivatives of dibenzoyl methane; derivatives of diphenyl acrylates; derivatives of benzofurans; UV filter polymers containing one or more silicoorganic residues; esters of cinnamic acid; derivatives of camphor; derivatives of trianilino-s-triazine; the ethylic ester urocanic acid; benzotriazoles; derivatives of hydroxy phenyl triazine; bis-resorcinol-dialkyl amino triazine; and mixtures thereof. The liposoluble (or lipophilic) organic UV filter can be chosen from octyl salicylate; 4-tert-butyl-4'-methoxy dibenzoyl methane; octocrylene; 4-methoxy cinnamate; 2-ethylhexyl[2-ethylhexyl 4-methoxycinnamate]; and 2-(2H-benzotriazol-2-yl)-4-methyl-6-[2-methyl-3-[1,3,3,3-tetramethyl-1-[(trimethyl silyl)oxy]disiloxanyl]propynyl]phenol. Other UV filters that may be useful are derivatives of benzophenones such as 2-hydroxy-4-methoxy benzophenone-5-sulfonic acid, 2-hydroxy-4-methoxy benzophenone, derivatives of benzalmalonates such as poly dimethyl/methyl(3(4-(2,2-bis-ethoxy carbonyl vinyl)-phenoxy)-propenyl)siloxane, derivatives of benzylidene camphor such as b-b' camphosulfonic [1-4 divinylbenzene] acid and derivatives of benzimidazole such as 2-phenyl-benzimidazol-5-sulfonic acid. Water-insoluble UV filters include various mineral oxides. The mineral oxides may be selected from among titanium oxides, zinc oxides, and cerium oxides. The mineral oxides can be used in the form of ultrafine nanoparticles. For example, the UV filters can include Escalol® HP-610 (dimethylpabamido propyl laurdimonium tosylate and propylene glycol stearate) or Crodasorb HP (polyquaternium 59).

The antioxidants or antiradical agents can be selected from phenols such as BHA (tert-butyl-4-hydroxy anisole), BHT (2,6-di-tert-butyl-p-cresol), TBHQ (tert-butyl hydroquinone), polyphenols such as proanthocyanodic oligomers, flavonoids, hindered amines such as tetra amino piperidine, erythorbic acid, polyamines such as spermine, cysteine, glutathione, superoxide dismutase, and lactoferrin.

The vitamins can be selected from ascorbic acid (vitamin C), vitamin E, vitamin E acetate, vitamin E phosphate, B vitamins such as B3 and B5, vitamin PP, vitamin A, and derivatives thereof. The provitamins can be selected from panthenol and retinol.

The protecting agent can be present in an amount from about 0.001% to about 20% by weight, particularly from about 0.01% to about 10% by weight, and more particularly from 0.1% to about 5% by weight of the total weight of the final composition.

The composition of the invention can contain a fixing agent in combination with the above-described polymer. The fixing agent can be an anionic polymer chosen from polymers containing carboxylic units derived from unsaturated carboxylic mono- or polyacids of the formula:

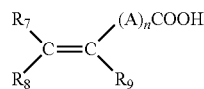

in which n is a whole number from 0 to 10, $A_1$ denotes a methylene group, optionally bonded to the carbon atom of the unsaturated group or to a neighboring methylene group when n is greater than 1 by means of a heteroatom like oxygen or sulfur, $R_7$ denotes a hydrogen atom, a phenyl or benzyl group, $R_8$ denotes a hydrogen atom, a lower alkyl or carboxyl group, $R_9$ denotes a hydrogen atom, a lower alkyl group, a —$CH_2$—COOH, phenyl or benzyl group and polymers containing units derived from sulfonic acid like vinylsulfonic, styrenesulfonic, acrylamidoalkylsulfonic units.

The fixing agent can be an amphoteric polymer chosen from the polymer containing recurring units derived from:
a) at least one monomer chosen from acrylamides or methacrylamides substituted on the nitrogen with an alkyl radical,
b) at least one acid copolymer containing one or more reactive carboxyl groups, and
c) at least one basic comonomer, such as esters with primary, secondary, tertiary, and quaternary amino substituents of acrylic and methacrylic acids and the product of quaternization of dimethylaminoethyl methacrylate with dimethyl or diethyl sulfate.

The fixing agent can be a nonionic polymer chosen from polyalkyloxazolines; vinyl acetate homopolymers; vinyl acetate and acrylic ester copolymers; vinyl acetate and ethylene copolymers; vinyl acetate and maleic ester copolymers; polyethylene and maleic anhydride copolymers; homopolymers of alkyl acrylates; homopolymers of alkyl methacrylates; copolymers of acrylic esters; copolymers of alkyl acrylates and alkyl methacrylates; copolymers of acrylonitrile and a nonionic monomer chosen from among butadiene and alkyl(meth)acrylates; copolymers of alkyl acrylate and urethane; and polyamides. The fixing agent can be a functionalized or unfunctionalized, silicone or non-silicone polyurethane. The fixing polymer can be a polymer of the grafted silicone type containing a polysiloxane portion and a portion consisting of a nonsilicone organic chain, with one of the two portions forming the main chain of the polymer, and with the other being grafted onto said main chain.

The fixing agent can be present in the composition in a relative weight concentration between about 0.1% to about 10%, for example, from about 0.5% to about 5%.

The personal care/cosmetic composition of the invention can contain an oxidizing agent in combination with the above-described polymer. The oxidizing agent can be chosen from the group of hydrogen peroxide, urea peroxide, alkali metal bromates, ferricyanides, persalts, and redox enzymes, optionally with their respective donor or cofactor. For example, the oxidizing agent can be hydrogen peroxide.

The oxidizing agent can be a solution of oxygenated water whose titer varies from 1 to 40 volumes.

The personal care/cosmetic composition of the invention can contain at least one reducing agent in combination with the above-described polymer in amounts from about 0.01% to about 30%, particularly from about 0.05% to about 20% of the total weight of the composition. The reducing agents can be selected from thiols, like cysteine, thioglycolic acid, thiolactic acid, their salts and esters, cysteamine, and its salts or sulfites. In the case of compositions intended for bleaching, ascorbic acid, its salts and its esters, erythorbic acid, its salts and its esters, and sulfinates, like sodium hydroxymethanesulfinate can be used.

The personal care/cosmetic composition of the invention can contain a dye in combination with the above-described polymer. The dye can be selected from the group consisting of neutral acid or cationic nitrobenzene dyes, neutral acid or cationic azo dyes, quinone dyes, neutral, acid or cationic anthraquinone dyes, azine dyes, triarylmethane dyes, indoamine dyes and natural dyes. The dye or dyes can be present in a concentration from about 0.001% to about 20%, and particularly from about 0.005% to about 10% based on the total weight of the composition.

The personal care/cosmetic composition of the invention can contain at least one amphoteric polymer or a cationic polymer in combination with the above-described polymer. Suitable cationic polymers include a poly(quaternary ammonium) consisting of recurrent units corresponding to the following formulae (W) and (U):

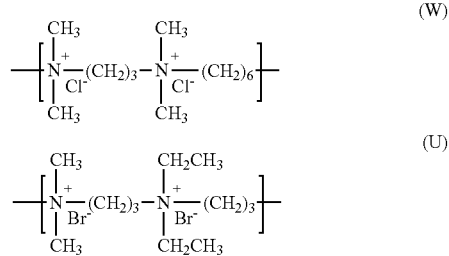

Suitable amphoteric polymers include a copolymer containing at least one acrylic acid and a dimethyldiallyammonium salt as a monomer. The cationic or amphoteric polymer or polymers can be present in an amount from about 0.01% to about 10%, particularly from about 0.05% to about 5%, and more particularly from about 0.1% to about 3% by weight of the total weight of the composition.

In addition, the personal care/cosmetic compositions can include at least one surfactant in combination with the above-described polymer. The surfactant can be present in an amount from about 0.1% to about 60%, particularly from about 1% to about 40%, and more particularly from about 5% to about 30% by weight based on the total weight of the composition. The surfactant may be chosen from among anionic, amphoteric, or non-ionic surfactants, or mixtures of them known to be useful in personal care/cosmetic compositions.

One or more suitable thickeners or viscosity increasing agents may be included in combination with the above-described polymer in the personal care/cosmetic compositions of the invention. Suitable thickeners and/or viscosity increasing agents include: Acetamide MEA; Acrylamide/Ethalkonium Chloride Acrylate Copolymer; Acrylamide/Ethyltrimonium Chloride Acrylate/Ethalkonium Chloride Acrylate Copolymer; Acrylamides Copolymer; Acrylamide/Sodium Acrylate Copolymer; Acrylamide/Sodium Acryloyldimethyltaurate Copolymer; Acrylates/Acetoacetoxyethyl Methacrylate Copolymer; Acrylates/Beheneth-25 Methacrylate Copolymer; Acrylates/C 10-30 Alkyl Acrylate Crosspolymer; Acrylates/Ceteth-20 Itaconate Copolymer; Acrylates/Ceteth-20 Methacrylate Copolymer; Acrylates/Laureth-25 Methacrylate Copolymer; Acrylates/Palmeth-25 Acrylate Copolymer; Acrylates/Palmeth-25 Itaconate Copolymer; Acrylates/Steareth-Acrylate Copolymer; Acrylates/Steareth-20 Itaconate Copolymer; Acrylates/Steareth-20 Methacrylate Copolymer; Acrylates/Stearyl Methacrylate Copolymer; Acrylates/Vinyl Isodecanoate Crosspolymer; Acrylic Acid/Acrylonitrogens Copolymer; Adipic Acid/Methyl DEA Crosspolymer; Agar; Agarose; Alcaligenes Polysaccharides; Algin; Alginic Acid; Almondamide DEA; Almondamidopropyl Betaine; Aluminum/Magnesium Hydroxide Stearate; Ammonium Acrylates/Acrylonitrogens Copolymer; Ammonium Acrylates Copolymer; Ammonium Acryloyldimethyltaurate/Vinyl Formamide Copolymer; Ammonium Acryloyldimethyltaurate/VP Copolymer; Ammonium Alginate, Ammonium Chloride; Ammonium Polyacryloyldimethyl Taurate; Ammonium Sulfate; Amylopectin; Apricotamide DEA; Apricotamidopropyl Betaine; Arachidyl Alcohol; Arachidyl Glycol; *Arachis Hypogaea* (Peanut) Flour; Ascorbyl Methylsilanol Pectinate; *Astragalus Gummifer* Gum; Attapulgite; *Avena Sativa* (Oat) Kernel Flour; Avocadamide DEA; Avocadamidopropyl Betaine, Azelamide MEA; Babassuamide DEA; Babassuamide MEA; Babassuamidopropyl Betaine; Behenamide DEA; Behenamide MEA, Behenamidopropyl Betaine; Behenyl Betaine; Bentonite; Butoxy Chitosan, *Caesalpinia Spinosa* Gum; Calcium Alginate; Calcium Carboxymethyl Cellulose; Calcium Carrageenan; Calcium Chloride; Calcium Potassium Carbomer; Calcium Starch Octenylsuccinate; C20-40 Alkyl Stearate; Canolamidopropyl Betaine; Capramide DEA; Capryl/Capramidopropyl Betaine; Carbomer; Carboxybutyl Chitosan; Carboxymethyl Cellulose Acetate Butyrate; Carboxymethyl Chitin; Carboxymethyl Chitosan; Carboxymethyl Dextran; Carboxymethyl Hydroxyethylcellulose; Carboxymethyl Hydroxypropyl Guar; Carnitine; Cellulose Acetate Propionate Carboxylate; Cellulose Gum; Ceratonia Siliqua Gum; Cetearyl Alcohol; Cetyl Alcohol; Cetyl Babassuate; Cetyl Betaine; Cetyl Glycol; Cetyl Hydroxyethylcellulose; Chimyl Alcohol; Cholesterol/HDI/Pullulan Copolymer; Cholesteryl Hexyl Dicarbamate Pullulan; Citrus *Aurantium Dulcis* (Orange) Peel Extract; Cocamide DEA; Cocamide MEA; Cocamide MIPA; Cocamidoethyl Betaine; Cocamidopropyl Betaine; Cocamidopropyl Hydroxysultaine; Coco-Betaine; Coco-Hydroxysultaine; Coconut Alcohol; Coco/Oleamidopropyl Betaine; Coco-Sultaine; Cocoyl Sarcosinamide DEA; Cornamide/Cocamide DEA; Cornamide DEA; Croscarmellose; Crosslinked Bacillus/Glucose/Sodium Glutamate Ferment; *Cyamopsis Tetragonoloba* (Guar) Gum; Decyl Alcohol; Decyl Betaine; Dehydroxanthan Gum; Dextrin; Dibenzylidene Sorbitol; Diethanolaminooleamide DEA; Diglycol/CHDM/Isophthalates/SIP Copolymer; Dihydroabietyl Behenate; Dihydrogenated Tallow Benzylmonium Hectorite; Dihydroxyaluminum Aminoacetate; Dimethicone/PEG-10 Crosspolymer; Dimethicone/PEG-15 Crosspolymer; Dimethicone Propyl PG-Betaine; Dimethylacrylamide/Acrylic Acid/Polystyrene Ethyl Methacrylate Copolymer; Dimethylacrylamide/Sodium Acryloyldimethyltaurate Crosspolymer; Disteareth-100 IPDI; DMAPA Acrylates/Acrylic Acid/Acrylonitrogens Copolymer; Erucamidopropyl Hydroxysultaine; Ethylene/Sodium Acrylate Copolymer; Gelatin; Gellan Gum; Glyceryl Alginate; *Glycine Soja* (Soybean) Flour; Guar Hydroxypropyltrimonium Chloride; Hectorite; Hyaluronic Acid; Hydrated Silica; Hydrogenated Potato Starch; Hydrogenated Tallow; Hydrogenated Tallowamide DEA; Hydrogenated Tallow Betaine; Hydroxybutyl Methylcellulose; Hydroxyethyl Acrylate/Sodium Acryloyldimethyl Taurate Copolymer; Hydroxyethylcellulose; Hydroxyethyl Chitosan; Hydroxyethyl Ethylcellulose; Hydroxyethyl Stearamide-MIPA; Hydroxylauryl/Hydroxymyristyl Betaine; Hydroxypropylcellulose; Hydroxypropyl Chitosan; Hydroxypropyl Ethylenediamine Carbomer; Hydroxypropyl Guar; Hydroxypropyl Methylcellulose; Hydroxypropyl Methylcellulose Stearoxy Ether; Hydroxypropyl Starch; Hydroxypropyl Starch Phosphate; Hydroxypropyl Xanthan Gum; Hydroxystearamide MEA; Isobutylene/Sodium Maleate Copolymer; Isostearamide DEA; Isostearamide MEA; Isostearamide MIPA; Isostearamidopropyl Betaine; Lactamide MEA; Lanolinamide DEA; Lauramide DEA; Lauramide MEA; Lauramide MIPA; Lauramide/Myristamide DEA; Lauramidopropyl Betaine; Lauramidopropyl Hydroxysultaine; Laurimino Bispropanediol; Lauryl Alcohol; Lauryl Betaine; Lauryl Hydroxysultaine; Lauryl/Myristyl Glycol Hydroxypropyl Ether; Lauryl Sultaine; Lecithinamide DEA; Linoleamide DEA; Linoleamide MEA; Linoleamide MIPA; Lithium Magnesium Silicate; Lithium Magnesium Sodium Silicate; *Macrocystis Pyrifera* (Kelp); Magnesium Alginate; Magnesium/Aluminum/Hydroxide/Carbonate; Magnesium Aluminum Silicate; Magnesium Silicate; Magnesium Trisilicate; Methoxy PEG-22/Dodecyl Glycol Copolymer; Methylcellulose; Methyl Ethylcellulose; Methyl Hydroxyethylcellulose; Microcrystalline Cellulose; Milkamidopropyl Betaine; Minkamide DEA; Minkamidopropyl Betaine; MIPA-Myristate; Montmorillonite; Moroccan Lava Clay; Myristamide DEA; Myristamide MEA; Myristamide MIPA; Myristamidopropyl Betaine; Myristamidopropyl Hydroxysultaine; Myristyl Alcohol; Myristyl Betaine; Natto Gum; Nonoxynyl Hydroxyethylcellulose; Oatamide MEA; Oatamidopropyl Betaine; Octacosanyl Glycol Isostearate; Octadecene/MA Copolymer; Oleamide DEA; Oleamide MEA; Oleamide MIPA; Oleamidopropyl Betaine; Oleamidopropyl Hydroxysultaine; Oleyl Betaine; Olivamide DEA; Olivamidopropyl Betaine; Oliveamide MEA; Palmamide DEA; Palmamide MEA; Palmamide MIPA; Palmamidopropyl Betaine; Palmitamide DEA; Palmitamide MEA; Palmitamidopropyl Betaine; Palm Kernel Alcohol; Palm Kernelamide DEA; Palm Kernelamide MEA; Palm Kernelamide MIPA; Palm Kernelamidopropyl Betaine; Peanutamide MEA; Peanutamide MIPA; Pectin; PEG-800; PEG-Crosspolymer; PEG-150/Decyl Alcohol/SMDI Copolymer; PEG-175 Diisostearate; PEG-190 Distearate; PEG-15 Glyceryl Tristearate; PEG-140 Glyceryl Tristearate; PEG-240/HDI Copolymer Bis-Decyltetradeceth-20 Ether; PEG-100/IPDI Copolymer; PEG-180/Laureth-50/TMMG Copolymer; PEG-10/Lauryl Dimethicone Crosspolymer; PEG-15/Lauryl Dimethicone Crosspolymer; PEG-2M; PEG-5M; PEG-7M; PEG-9M; PEG-14M; PEG-20M; PEG-23M; PEG-25M; PEG-45M; PEG-65M; PEG-90M; PEG-115M; PEG-160M; PEG-180M; PEG-120 Methyl Glucose Trioleate; PEG-180/Octoxynol-40/TMMG Copolymer; PEG-150 Pentaerythrityl Tetrastearate; PEG-4 Rapeseedamide; PEG-150/Stearyl Alcohol/SMDI Copolymer; *Phaseolus Angularis* Seed Powder; *Polianthes Tuberosa* Extract; Polyacrylate-3; Polyacrylic Acid; Polycyclopentadiene; Polyether-1; Polyethylene/Isopropyl Maleate/MA Copolyol; Polyglyceryl-3 Disiloxane Dimethicone; Polyglyceryl-3 Polydimethylsiloxyethyl Dimethicone; Polymethacrylic Acid; Polyquaternium-52; Polyvinyl Alcohol; Potassium Alginate; Potassium Aluminum Polyacrylate; Potassium Carbomer; Potassium Carrageenan; Potassium Chloride; Potassium Palmate; Potassium Polyacrylate; Potassium Sulfate; Potato Starch Modified; PPG-2 Cocamide; PPG-1 Hydroxyethyl Caprylamide; PPG-2 Hydroxyethyl Cocamide; PPG-2 Hydroxyethyl Coco/Isostearamide; PPG-3 Hydroxyethyl Soyamide; PPG-14 Laureth-60 Hexyl Dicarbamate; PPG-14 Laureth-60 Isophoryl Dicarbamate; PPG-14 Palmeth-60 Hexyl Dicarbamate; Propylene Glycol Alginate; PVP/Decene Copolymer; PVP Montmorillonite; *Pyrus Cydonia* Seed; *Pyrus Malus* (Apple) Fiber; Rhizobian Gum; Ricebranamide DEA; Ricinoleamide DEA; Ricinoleamide MEA; Ricinoleamide MIPA; Ricinoleamidopropyl Betaine; Ricinoleic Acid/Adipic Acid/AEEA Copolymer; Rosa Multiflora Flower Wax; Sclerotium Gum; Sesamide DEA; Sesamidopropyl Betaine; Sodium Acrylate/Acryloyldimethyl Taurate Copolymer; Sodium Acrylates/Acrolein Copolymer; Sodium Acrylates/Acrylonitrogens Copolymer; Sodium Acrylates Copolymer; Sodium Acrylates Crosspolymer; Sodium Acrylate/Sodium Acrylamidomethylpropane Sulfonate Copolymer; Sodium Acrylates/Vinyl Isodecanoate Crosspolymer; Sodium Acrylate/Vinyl Alcohol Copolymer; Sodium Carbomer; Sodium Carboxymethyl Chitin; Sodium Carboxymethyl Dextran; Sodium Carboxymethyl Beta-Glucan; Sodium Carboxymethyl Starch; Sodium Carrageenan; Sodium Cellulose Sulfate; Sodium Chloride; Sodium Cyclodextrin Sulfate; Sodium Hydroxypropyl Starch Phosphate; Sodium Isooctylene/MA Copolymer; Sodium Magnesium Fluorosilicate; Sodium Oleate; Sodium Palmitate; Sodium Palm Kernelate; Sodium Polyacrylate; Sodium Polyacrylate Starch; Sodium Polyacryloyldimethyl Taurate; Sodium Polygamma-Glutamate; Sodium Polymethacrylate; Sodium Polystyrene Sulfonate; Sodium Silicoaluminate; Sodium Starch Octenylsuccinate; Sodium Stearate; Sodium Stearoxy PG-Hydroxyethylcellulose Sulfonate; Sodium Styrene/Acrylates Copolymer; Sodium Sulfate; Sodium Tallowate; Sodium Tauride Acrylates/Acrylic Acid/Acrylonitrogens Copolymer; Sodium Tocopheryl Phosphate; *Solanum Tuberosum* (Potato) Starch; Soyamide DEA; Soyamidopropyl Betaine; Starch/Acrylates/Acrylamide Copolymer; Starch Hydroxypropyltrimonium Chloride; Stearamide AMP; Stearamide DEA; Stearamide DEA-Distearate; Stearamide DIBA-Stearate; Stearamide MEA; Stearamide MEA-Stearate; Stearamide MIPA; Stearamidopropyl Betaine; Steareth-60 Cetyl Ether; Steareth-100/PEG-136/HDI Copolymer; Stearyl Alcohol; Stearyl Betaine; Sterculia Urens Gum; Synthetic Fluorphlogopite; Tallamide DEA; Tallow Alcohol; Tallowamide DEA; Tallowamide MEA; Tallowamidopropyl Betaine; Tallowamidopropyl Hydroxysultaine; Tallowamine Oxide; Tallow Betaine; Tallow Dihydroxyethyl Betaine; *Tamarindus Indica* Seed Gum; Tapioca Starch; TEA-Alginate; TEA-Carbomer; TEA-Hydrochloride; Trideceth-2 Carboxamide MEA; Tridecyl Alcohol; Triethylene Glycol Dibenzoate; Trimethyl Pentanol Hydroxyethyl Ether; *Triticum Vulgare* (Wheat) Germ Powder; *Triticum Vulgare* (Wheat) Kernel Flour; *Triticum Vulgare* (Wheat) Starch; Tromethamine Acrylates/Acrylonitrogens Copolymer; Tromethamine Magnesium Aluminum Silicate; Undecyl Alcohol; Undecylenamide DEA; Undecylenamide MEA; Undecylenamidopropyl Betaine; Welan Gum; Wheat Germamide DEA; Wheat Germamidopropyl Betaine; Xanthan Gum; Yeast Beta-Glucan; Yeast Polysaccharides and *Zea Mays* (Corn) Starch.

In one such embodiment, the thickeners or viscosity increasing agents include carbomers, Aculyn™ and Stabileze®, e.g., crosslinked acrylic acid, crosslinked poly (methylvinyl ether/maleic anhydride) copolymer, acrylamides, carboxymethyl cellulose, and the like.

The personal care/cosmetic compositions may be used to wash and treat keratinous material such as hair, skin, eyelashes, eyebrows, fingernails, lips, and hairy skin.

The personal care/cosmetic compositions can be detergent compositions such as shampoos, bath gels, and bubble baths. In this mode, the compositions will comprise a generally aqueous washing base. The surfactant or surfactants that form the washing base may be chosen alone or in blends, from known anionic, amphoteric, or non-ionic surfactants. The quantity and quality of the washing base must be sufficient to impart a satisfactory foaming and/or detergent value to the final composition. The washing base can be from about 4% to about 50% by weight, particularly from about 6% to about 35% by weight, and even more particularly from about 8% to about 25% by weight of the total weight of the final composition.

The pH of the composition applied to the keratinous material is generally between 2 and 12. In one embodiment, the pH is from about 3 to about 8, and may be adjusted to the desired value by means of acidifying or alkalinizing agents that are well known in the state of the art. Thus, the composition of the invention can contain at least one alkalizing or acidifying agent in amounts from about 0.01% to about 30% based on the total weight of the composition.

The alkalizing agent can be chosen from ammonia, alkali carbonates, alkanolamines, like mono-, di- and triethanolamines, as well as their derivatives, hydroxyalkylamines and ethoxylated and/or propoxylated ethylenediamines, sodium or potassium hydroxides and compounds of the following formula:

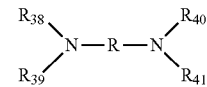

in which R is a propylene residue optionally substituted with an hydroxyl group or a $C_1$-$C_4$ alkyl radical; $R_{38}$, $R_{39}$, $R_{40}$ and $R_{41}$, identical or different, represent a hydrogen atom, a $C_1$-$C_4$ alkyl radical or $C_1$-$C_4$ hydroxyalkyl radical.

The acidifying agent can be chosen from mineral or organic acids, like hydrochloric acid, orthophosphoric acid, carboxylic acids like tartaric acid, citric acid, or lactic acid, or sulfonic acids, and the like.

The personal care/cosmetic compositions of the invention may include a physiological and cosmetically acceptable medium. Such medium may consist exclusively of water, a cosmetically acceptable solvent, or a blend of water and a cosmetically acceptable solvent, such as a lower alcohol composed of $C_1$ to $C_4$, such as ethanol, isopropanol, t-butanol, n-butanol, alkylene glycols such as propylene glycol, and glycol ethers. Alternatively, the personal care/cosmetic compositions can be anhydrous.

Generally, personal care/cosmetic compositions can be prepared by simple mixing procedures well known in the art. The invention provides a method for treating keratinous material including the skin or hair, by applying to skin or keratinous materials a personal care/cosmetic composition as described above, and then eventually rinsing it with water. Accordingly, the method makes it possible to maintain the hairstyle, treatment, care, washing, or make-up removal of the skin, the hair, and any other keratinous material. The personal care/cosmetic compositions may also take the form of after-shampoo compositions, to be rinsed off or not, for permanents, straightening, waving, dyeing, or bleaching, or the form of rinse compositions to be applied before or after dyeing, bleaching, permanents, straightening, relaxing, waving or even between the two stages of a permanent or straightening process. The personal care/cosmetic compositions may also take the form of skin-washing compositions, and particularly in the form of solutions or gels for the bath or shower, or of make-up removal products. The personal care/cosmetic compositions may also be in the form of aqueous or hydro-alcoholic solutions for skin and/or hair care. The personal care/cosmetic compositions described herein are useful in personal care/cosmetic products, including, but not limited to, gels, lotions, glazes, glues, mousses, sprays, fixatives, shampoos, conditioners, 2-in-1 shampoos, temporary hair dyes, semi-permanent hair dyes, permanent hair dyes, straighteners, permanent waves, relaxers, creams, putties, waxes, pomades, moisturizers, mascaras, lip balms and foam enhancers.

The modified polymers can be prepared according to the examples set out below. The examples are presented for purposes of demonstrating, but not limiting, the preparation of the compounds and compositions of this invention.

EXAMPLES

The following non-limiting examples are provided to illustrate a few of the methods for preparing novel 4- and 5-substituted 1,2,3-triazoles, and regioisomer mixtures thereof, modified polymers.

Example 1

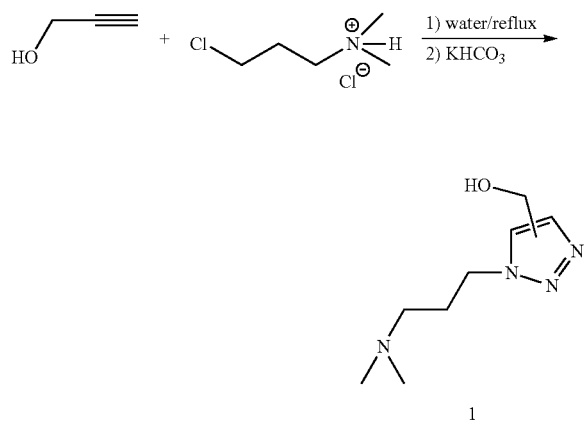

A 2-L, 4-neck, round-bottom flask was equipped with a mechanical mixer, thermometer, condenser, air purge and a hot oil bath with temperature probe and controller. An air purge was maintained. Sodium azide (100 grams) and water (490 grams) were charged to the flask. The azide was fully dissolved before adding the amine (221 grams). The amine was also fully dissolved in the aqueous solution. The solution turned hazy orange with this addition. The oil bath was preheated to 100° C. Propargyl alcohol (15.67 grams) was added at t=0. The reaction flask was placed in the hot oil bath with mixing. At reflux, the reaction became a clear orange solution. Refluxing was maintained for 25 hours. All during the reaction, air flowed through the flask as a purge. The reaction temperature at reflux was maintained at 102° C.-103° C., even with the air purge. Over the first hour of refluxing, the reaction solution changed from orange to a clear light gold color. Propargyl alcohol (15.67 grams) was added again at 2, 3, 4 and 5 hours from t=0. The color changed to clear dark amber after refluxing 25 hours. The reaction was transferred to a single-neck two liter round bottom flask. Water was stripped from the reaction solution on the roto-evaporator at 80° C. and 30 Torr (final). This resulted in viscous amber oil choked with salt. After cooling, 500 mL of methanol was added to the oil and the mixture was mechanically mixed for 30 minutes. The oil readily dissolved. The methanol was stripped-off on the roto-evaporator at 80° C. and 55 Torr (final). A viscous amber oil with solids remained. Methanol (500 mL) was added and the mixture was mechanically mixed for 30 minutes. The oil readily dissolved. The salts were filtered and rinsed with methanol. The methanol was stripped-off on the roto-evaporator at 80° C. and 55 Torr (final). A viscous and hazy amber oil remained. Methanol (300 mL) was added and the mixture was mechanically mixed and chilled in an ice bath. The remaining salts were filtered out and the methanol et al. were stripped off. The resulting product was a viscous amber "tar." A quantity of 219 grams was collected representing a 72% yield of protonated intermediate. Fifty grams of the intermediate and 250 mL of ethyl acetate were charged to a 1-L, 4-neck, round bottom flask equipped with mechanical mixer, thermometer and bubbler. The contents were mixed for 30 minutes and a reaction temperature of 28-31° C. was maintained. Next, KHCO$_3$ (125 grams) was added to the mixture at t=0 hours and mixing was continued. At t=4 hours, product was detected via GC. A second addition of 125 grams of KHCO$_3$ was then added. The reaction was mixed overnight and the reaction was a gold-yellow mixture. The mixture was filtered to remove salts and the salts were rinsed with ethyl acetate to a total reaction solution volume of 750 mL. At this point, the reaction was a cloudy yellow solution. Magnesium sulfate (40 grams) was added to dehydrate and the mixture was mixed for one hour. The reaction mixture was filtered and the solution stripped at 80° C. to 30 Torr (final). The result was 29 grams (58% yield) of a clear gold deprotonated oil product. NMR results confirmed the identity of the product, designated as compound 1.

Example 2

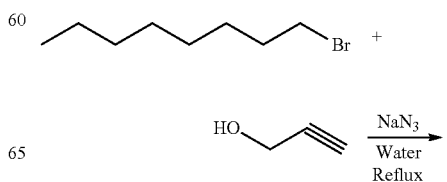

-continued

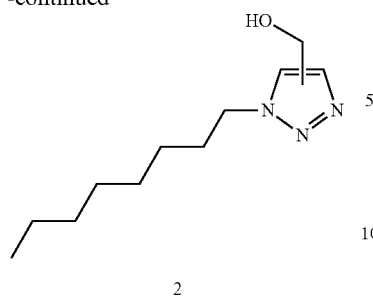

2

A 500-mL, round bottom, 4-neck reaction flask equipped with mechanical stirrer, air supply, oil bath with temperature probe and controller, and reflux condenser was charged with water (103.0 grams). With mixing, sodium azide (25.0 grams, 0.3845 mol), bromooctane (67.49 grams, 0.3495 mol) and propargyl alcohol (5.2 grams) were added. The flask was then purged continuously with air to sweep hydrazoic acid gas out of the flask as it formed. The purge was maintained during the reaction. The reaction was heated at reflux for 25 hours within a temperature range of 100° C.-104° C. Aliquots of propargyl alcohol were added during the first six hours of refluxing. At 2 hours into the reaction, 5.2 grams were added followed by 5.2 grams each at 3, 4, 5, and 6 hours. At the end of 24 hours of refluxing, the reaction emulsion was transferred to a separatory funnel. 500 mL of water was added and mixed. Then, 200 mL of brine were added to promote phase separation. After 1.5 hours, the mixture separated into two phases: a top thick opaque dark gold phase and a bottom cloudy yellow phase. The bottom aqueous phase was discarded. The top organic phase was charged to a 500-mL, 4-neck, round bottom flask equipped with a mechanical mixer. Hexane (50 mL) and water (50 mL) were added to the flask and the contents were mixed mechanically (at 500 rpm) for 40 minutes. The resulting emulsion was then transferred back to a separatory funnel where it was left to phase separate. Brine (50 mL) was added to aid in separation. Three phases eventually formed (top=hexane, colorless, middle=product dark, bottom=aqueous cloudy yellow). The top and bottom phases were discarded, and the dark middle layer was collected. The middle layer was evaporated at 80° C. for 1 hour. Three portions of water (10 mL each) were added to the product phase and then stripped off sequentially at 95° C. for 2.5 hours. The product phase was added to a 4-neck, round bottom flask charged with 250 mL hexane and mixed well overnight. The hexane layer was decanted off (no product in hexane was detected by GC). The solids were filtered out resulting in phased-out oil/hexane mix (B) and light colored crystals (A). The solids were dissolved in 250 mL of ethyl acetate and the resulting clear gold solution was added to mix (B). The resulting solution (about 300 mL) was then washed with 300 mL brine by mechanical mixing in a flask for 30 minutes. The mix phased-separated quickly. The top organic phase (ethyl acetate+product) was collected and charged to a round bottom flask. Silica gel (70 grams) was added and the mixture was mixed rigorously for 30 minutes. The mix was filtered resulting in a clear gold solution. The solution was stripped of solvent leaving a clear gold oil. The oil slowly became a soft gold crystalline form, which exhibited two DSC melt points at 17° C. and 37° C. suggesting 1,4 and 1,5 triazole isomers. NMR results confirmed the identity of the product, designated as compound 2.

Example 3

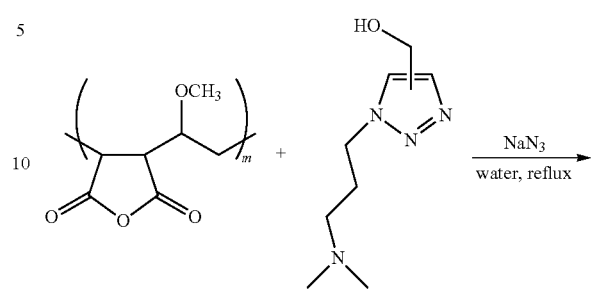

1.00:0.10, respectively

A quantity of 116.0 grams (0.8287 mol) of poly(methyl vinyl ether-co-maleic anhydride) polymer (Gantrez® AN-119, International Specialty Products, Wayne, N.J.) having a nominal molecular weight of about 200,000 Da, and 270 mL of ethyl acetate were charged into a 1-L, 4-neck, round-bottom flask equipped with a mechanical mixer, thermometer, slow-addition (SA) funnel and bubbler. Mixing was initiated at moderate speed to form an ivory-white cream having a thick consistency. Then, 15.0 grams (0.08287 mol) of compound 1 (Example 1) were dissolved in 45 grams of ethyl acetate and charged into the clear amber solution via the SA funnel over 30 minutes at room temperature (25° C.-30° C.). With the addition, the reaction solids changed from a thick ivory-white cream to a light-orange slurry. After adding 12% of the solution of compound 1, the reaction mixture appeared to coagulate. With further addition to a total of about 18% of 1 solution, the reaction mixture assumed a lower viscosity ("soupy") having a bright-pink color. This appearance and consistency remained through the entire thirty-minute addition and during hold period of one hour. No exotherm was observed. The reaction was monitored by observing the disappearance of compound 1 over time (18.76 minutes) via gas chromatography (GC). The reaction was mixed overnight at room temperature. The reaction was filtered and a light-pink product filter cake was collected. The filtrate was clear and colorless. The solids were then rinsed with ethyl acetate, air dried in the exhaust hood and oven-dried at 50° C. under vacuum overnight. The yield for this reaction was 118 grams of a light pink powder. NMR and FT-IR confirmed the composition of this modified polymer.

Example 4

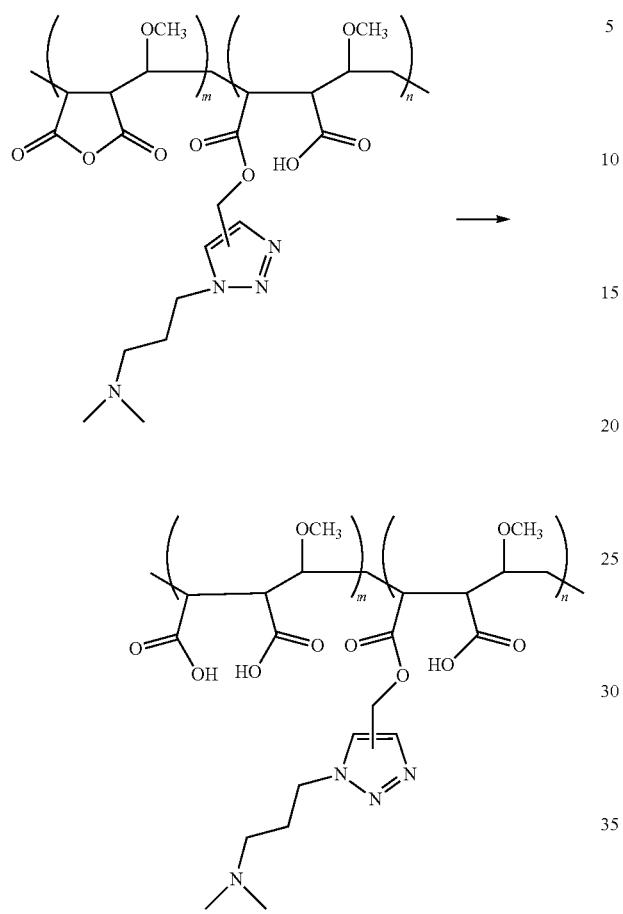

A quantity of 50.0 grams (0.1010 mole) of polymer product from Example 3 and 170 mL of distilled water were charged to a 500-mL, 4-neck, round-bottom flask equipped with a mechanical mixer, thermometer and bubbler. These ingredients were mixed at moderate speed to form a pink mixture having a pH of about 8.5. After a total of 60 minutes of mixing, the reaction had a "slimy" viscous consistency with a pH about around 2.0. Relative levels of compound 1 were monitored by gas chromatography (18.76 minutes) during the reaction process to determine the extent of triazole cleaving from the polymer backbone. The reaction was left to settle and partition to a clear, pink filtrate over a viscous pink "syrup." The filtrate was decanted from the syrup (190 mL), which was then added to 1 L of vigorously mixing methyl acetate. The syrup was mixed, dispersed and washed in the methyl acetate for 30 minutes. The mixture was left to partition again and the cloudy light pink liquid was decanted off the syrup. The syrup was again mixed in 1 L of methyl acetate for 30 minutes. At this point, a change in the property of the hydrolyzed polymer product from Example 3 was noted. This was likely due to the displacement of water by methyl acetate. Instead of a syrup, the hydrolyzed product now physically resembled a hard pink putty. The cloudy light pink solvent was decanted from the "putty" solids. The solids were collected, air-dried in a hood and then placed under vacuum at room temperature overnight. Yield for this reaction was 48 grams of a light pink powder from 50 grams of starting material. NMR and FT-IR confirmed the composition of this modified polymer.

Example 5

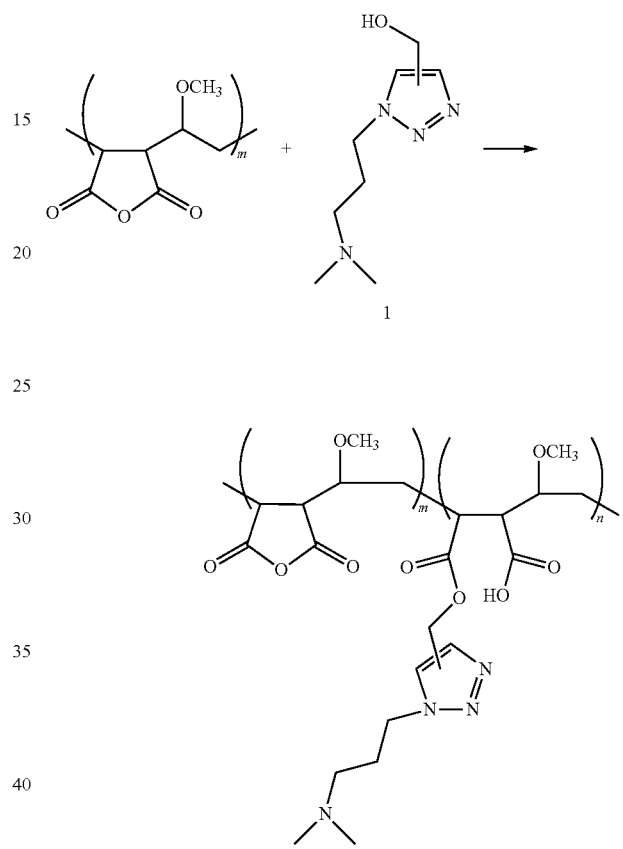

1.00:0.20, respectively.

A quantity of 58.0 grams (1.0 eq.) of poly(methyl vinyl ether-co-maleic anhydride) polymer (Gantrez® AN-119, International Specialty Products, Wayne, N.J.) having a nominal molecular weight of about 200,000 Da was dissolved in 120 mL ethyl acetate and charged in to 1-L, 4 neck round bottom flask equipped with a mechanical mixer, thermometer, slow-addition (SA) funnel and bubbler. Then, 15 grams (0.2 eq.) of the mixture of compound 1 was dissolved in 38 grams of ethyl acetate and charged to the SA funnel. Mixing was initiated at room temperature, and the mixture of 1 solution was added evenly over a period of thirty minutes. No exotherm was observed. The appearance/disappearance of residual mixture of compound 1 was followed via GC. Mixing continued at moderate to fast speed for another hour. Then, the product precipitated, which was filtered and washed. This solid was air-dried, followed by oven drying at 60° C. under vacuum overnight. NMR and IR confirmed the composition of this modified polymer.

Example 6

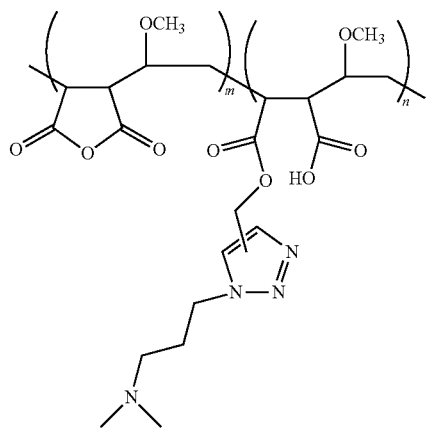

1.00:0.30, respectively.

A quantity of 38.7 grams (0.2764 mol) of poly(methyl vinyl ether-co-maleic anhydride) polymer (Gantrez® AN-119, International Specialty Products, Wayne, N.J.) having a nominal molecular weight of about 200,000 Da, and 89 mL of ethyl acetate were charged in to a 1-L, 4-neck, round-bottom flask equipped with a mechanical mixer, thermometer, slow-addition (SA) funnel and bubbler. Mixing was initiated at moderate speed to an ivory-white cream having a thick consistency. Then, 15.0 grams (0.0829 mol) of compound 2 (Example 2) was dissolved in 38 grams of ethyl acetate and this clear amber solution was charged via the SA funnel over forty minutes at room temperature (25° C.-30° C.). Initially, the reaction solids were a creamy light gold color. However, with 31% of the 2 solution added, the reaction mixture was a loose, pink slurry. This appearance and consistency remained through the entire thirty-minute addition and a hold period of one hour. No exotherm was observed. The reaction was monitored by observing the disappearance of 2 over time via gas chromatography (GC). At the end of the hold period, the reaction was filtered. A pink powder cake was collected in the filter funnel and the hazy yellow filtrate was sampled for GC analysis. The solids were rinsed with ethyl acetate, air dried and then oven-dried at 60° C. under vacuum overnight. The yield for this reaction was 48 grams of a very light tan powder. NMR and IR confirmed the composition of this modified polymer.

Example 7

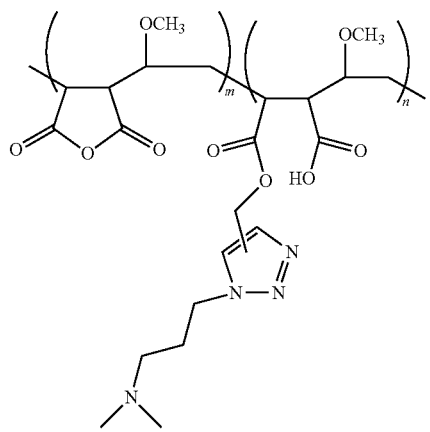

1.00:0.40, respectively.

A quantity of 60.0 grams (0.4286 mol) of poly(methyl vinyl ether-co-maleic anhydride) polymer (Gantrez® AN-119, International Specialty Products, Wayne, N.J.) having a nominal molecular weight of about 200,000 Da, and 117 mL of ethyl acetate were charged in to a 1-L, 4-neck, round-bottom flask equipped with a mechanical mixer, thermometer, slow-addition (SA) funnel and bubbler. Mixing was initiated at moderate speed to form an ivory-white cream having a thick consistency. Then, 31.0 grams (0.1714 mol) of compound 2 were dissolved in 85 mL of ethyl acetate, and this clear amber solution was charged via the SA funnel at room temperature (25-30° C.) over forty-five minutes. Initially, the reaction solids looked dry and crumbled with mixing. However, with 11% of 2 solution added, the reaction mixture was a loose, pink slurry. This appearance and consistency remained through the entire thirty-minute addition and a hold period of one hour. No exotherm was observed. The reaction was monitored by observing the disappearance of 2 over time via gas chromatography (GC). At the end of the hold period, the reaction was filtered. A pink-orange powder cake was collected in the filter funnel and the clear yellow filtrate was sampled for GC analysis. The solids were rinsed with ethyl acetate, air dried and then oven-dried at 60° C. under vacuum overnight. The yield for this reaction was 79.0 grams of a tan powder. NMR and FTIR confirmed the composition of this modified polymer.

Example 8

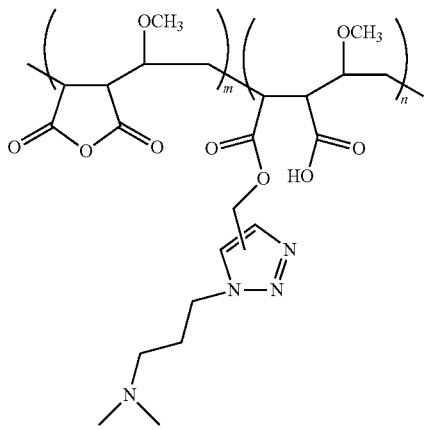

1.00:0.50, respectively.

A quantity of 58.0 grams (0.4143 mol, 1.0 eq.) of poly (methyl vinyl ether-co-maleic anhydride) polymer (Gantrez® AN-119, International Specialty Products, Wayne, N.J.) having a nominal molecular weight of about 200,000 Da was dissolved in 120 mL of ethyl acetate and charged to 1-L, 4-neck, round bottom flask equipped with a mechanical mixer, thermometer, slow-addition (SA) funnel and bubbler. Then, 15 grams (0.2 eq., 0.0829 mol) of compound 2 was dissolved in 38 grams of ethyl acetate and charged via the SA funnel at room temperature over thirty minutes. No exotherm was observed. The presence of residual compound 2 was followed via GC. Mixing was continued at moderate to fast speed for another hour. At this point the product precipitated from solution, was air dried, and then oven dried overnight at 60° C. under vacuum. NMR and IR confirmed the composition of this modified polymer.

Example 9

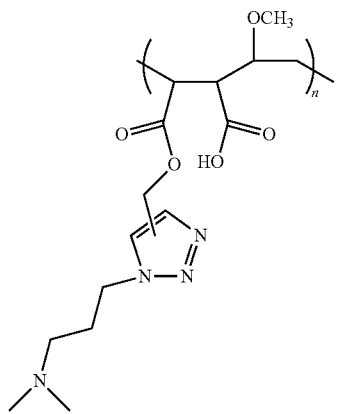

1.00:1.00, respectively.

A quantity of 58.0 grams (1.0 eq., 0.4143 mol) of poly(methyl vinyl ether-co-maleic anhydride) polymer (Gantrez® AN-119, International Specialty Products, Wayne, N.J.) having a nominal molecular weight of about 200,000 Da was dissolved in 120 mL of ethyl acetate and charged in to 1-L, 4-neck, round bottom flask equipped with a mechanical mixer, thermometer, slow-addition (SA) funnel and bubbler. Then, 75 grams (1.0 eq., 0.4143 moles) of compound 2 were dissolved in 38 grams of ethyl acetate and charged via the SA funnel at room temperature over thirty minutes. No exotherm was observed. The presence of residual compound 2 was followed via GC. Mixing was continued at moderate to fast speed for another hour. At this point the product precipitated, which was filtered, washed, air dried, and then oven dried overnight at 60° C. under vacuum. NMR and IR confirmed the composition of this modified polymer.

Example 10

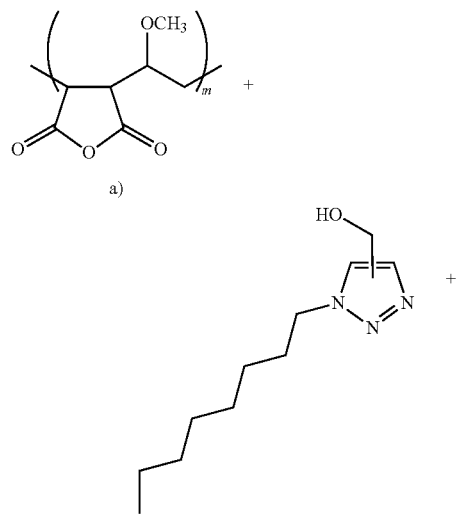

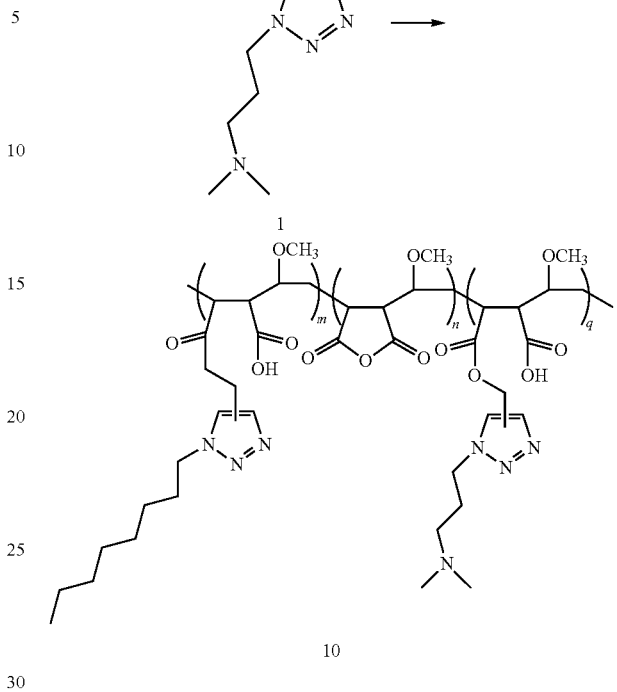

A quantity of 116.02 grams (0.8287 mol) of poly(methyl vinyl ether-co-maleic anhydride) polymer (Gantrez® AN-119, International Specialty Products, Wayne, N.J.) having a nominal molecular weight of about 200,000 Da was charged with 270 mL of ethyl acetate to a 2-L, 4-neck, round-bottom flask equipped with a mechanical mixer, thermometer, slow-addition (SA) funnel and bubbler. Mixing was initiated at moderate speed to an ivory-white cream having a thick consistency formed. Then, a solution of 13.93 grams of compound 2 (Example 2) dissolved in 30 mL of ethyl acetate was charged to the flask. The color of the reaction mixture changed to a light gold. Following this addition, a solution of compound 1 (Example 1) (3.07g) dissolved in 45 mL of ethyl acetate was charged to the slow-add funnel and slow-added over 30 minutes at room temperature. During the addition, the appearance and consistency of the reaction mixture changed. An exotherm was not observed. During the first 20 minutes, pink granules formed in the light gold mixture. With 27% of the 1 solution added, the smooth dark tan reaction solids became mealy and then cheesy-looking (lumpy like cottage cheese). However, with all of the 1 solution added, the reaction mixture changed to a soupy caramel color with dark pink granules. The reaction was held at room temperature for 1.5 hours with mixing. Ethyl acetate (300 mL) was added 1 hour after the slow-addition. At this point, the reaction mixture was a soupy red color. Mixing was continued for another hour at room temperature. The reaction was heated to reflux (62° C.) within 10 minutes. Refluxing was continued for 2 hours. Another 0.02 eq. (3.07 grams) of compound 1 was then added to catalyze the reaction. Refluxing (79° C.) was continued for another hour after the catalyst addition. The reaction became a mixture of red and pink granules and was left to mix slowly overnight at room temperature. The following day, the reaction mixture was refluxed at 78° C. with mixing for an additional 5 hours. The product was sticky red granules.

The reaction mixture was cooled and mixed hard. A cloudy dark red ethyl acetate reaction solution was slowly decanted from mushy dark pink solids left in the flask. Methyl acetate (1 L) was added to the solids and the mixture was again mixed hard for 2 hours. Dark red solvent was then decanted from dark pink solids remaining in the flask. This time, ethyl acetate (1 L) was added to the solids and the mixture was thoroughly mixed for 30 minutes. Upon filtering, the filtrate was clear and colorless. The red-pink granular product was collected, air-dried in the exhaust hood overnight and then dried under vacuum at 25° C. Dark pink granular solids (41 grams) were collected from this reaction. NMR and FT-IR confirmed the composition of this modified polymer, designated as compound 10.

Example 11

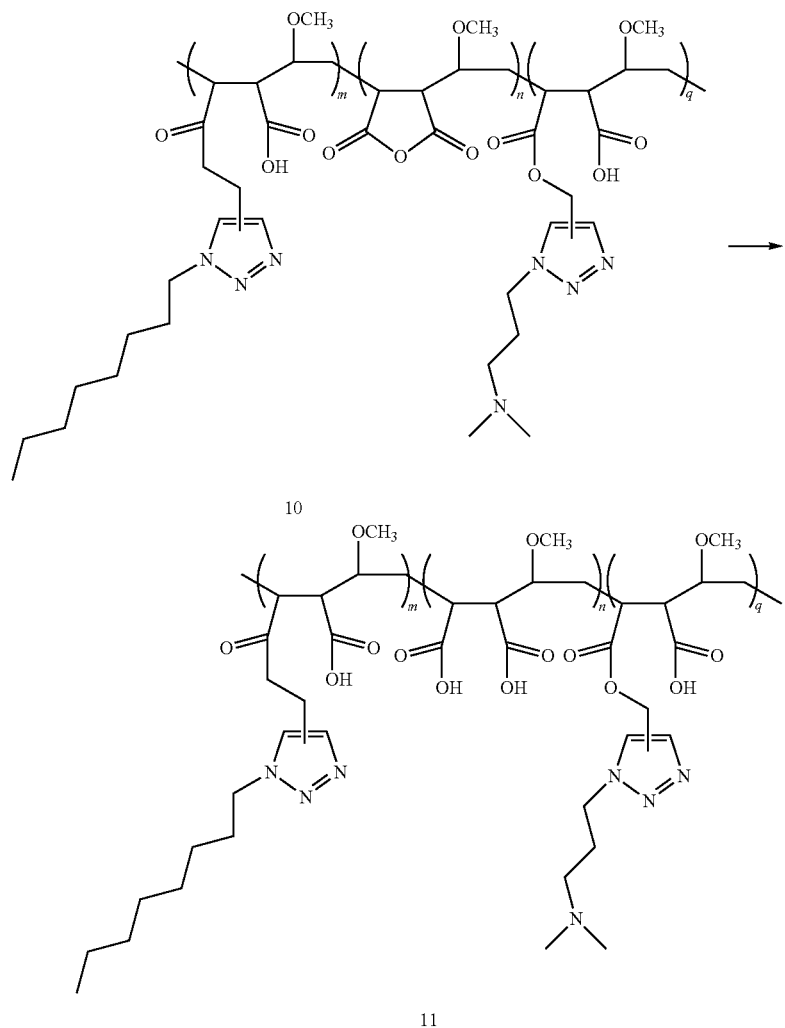

A quantity of 15.0 grams of compound 10 and 55 grams of distilled water were charged to a 500 mL, 4-neck, round-bottom flask equipped with a mechanical mixer, thermometer and bubbler. Mixing occurred at moderate speed to form a foamy purple mixture having a pH of about 7.0. After a total of 60 minutes of mixing, the clear pink reaction solution with a pH of about 4.5 was decanted off, leaving a dark pink solid intermediate. Relative levels of 1 and 2 isomers were monitored by gas chromatography (~18.76 and ~21.7 minutes, respectively) during the reaction process to determine the extent of triazole cleaving from the polymer backbone. Methyl acetate (200 mL) was added to the solids and the reaction was mixed for 20 minutes. At this point, the reaction consisted of a light purple sediment in a cloudy purple liquid in a 500 mL reaction flask. Water (100 mL) was added to the mixture and it was mixed for one hour. The result was an opaque purple liquid totaling 320 mL. The reaction mixture was added to an equivalent volume (320 mL) of ethyl acetate with 15 minutes of mixing. The reaction was now an opaque pink mixture. The reaction was left to settle and partition to a dark red filtrate over pink amorphous "syrup." The filtrate was decanted from the "syrup". The syrup was placed in a glass dish and air-dried in an exhaust hood. After sufficiently drying, the solids were collected, air-dried in a hood and then placed under vacuum at room temperature overnight. The yield for this reaction was 11.1 g of a light pink powder from 15.0 g from compound 10. NMR and FT-IR confirmed the composition of this modified polymer, designated as compound 11.

While a number of embodiments of this invention have been represented, it was apparent that the basic construction can be altered to provide other embodiments that utilize the invention without departing from the spirit and scope of the invention. All such modifications and variations are intended to be included within the scope of the invention as defined in the appended claims rather than the specific embodiments that have been presented by way of example.

We claim:

1. A composition comprising a 4- or 5-substituted 1,2,3-triazole, or regioisomer mixtures thereof, modified polymer, wherein the substituted 1,2,3-triazole is modified by a modifying polymer represented by the structure:

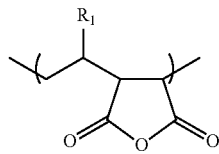

wherein $R_1$ is selected from the group consisting of hydrogen, functionalized and unfunctionalized alkyl, alkoxy, cycloalkyl, alkenyl, and aryl groups, wherein any of the before mentioned groups may be with or without heteroatoms, and mixtures thereof, wherein the composition is selected from the group consisting of adhesive compositions, aerosol compositions, agricultural compositions, beverage compositions, biocide compositions, cleaning compositions, coating compositions, cosmetic, dental compositions, detergent compositions, drug compositions, electronic compositions, encapsulation compositions, food compositions, hair spray compositions, household-industrial-institutional ink compositions, lithographic solution compositions, membrane compositions, metal fluid compositions, oilfield compositions, paint compositions, paper compositions, personal care compositions, pharmaceutical compositions, plaster compositions, plastic compositions, printing compositions, wood-care compositions, and mixtures thereof.

2. The composition according to claim 1, wherein the 4- or 5-substituted 1,2,3-triazole, or regioisomer mixtures thereof, are represented by the structures, respectively:

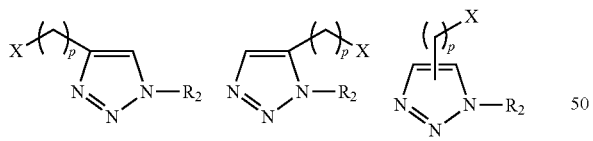

wherein X is OH or $NHR_2$; each $R_2$ is independently selected from the group consisting of hydrogen, functionalized and unfunctionalized alkyl, alkoxy cycloalkyl, alkenyl, and aryl groups, wherein any of the before mentioned groups may be with or without heteroatoms, and mixtures thereof; and each p is an integer independently ranging from 1 to about 50.

3. The composition according to claim 2, wherein $R_2$ is selected from the group consisting of hydrogen and functionalized and unfunctionalized alkyl and alkoxy groups, wherein any of the before mentioned groups may be with or without heteroatoms, and mixtures thereof; X is OH; and each p is an integer independently ranging from 1 to about 6.

4. The composition according to claim 1, wherein the modified polymer is selected from the group consisting of:

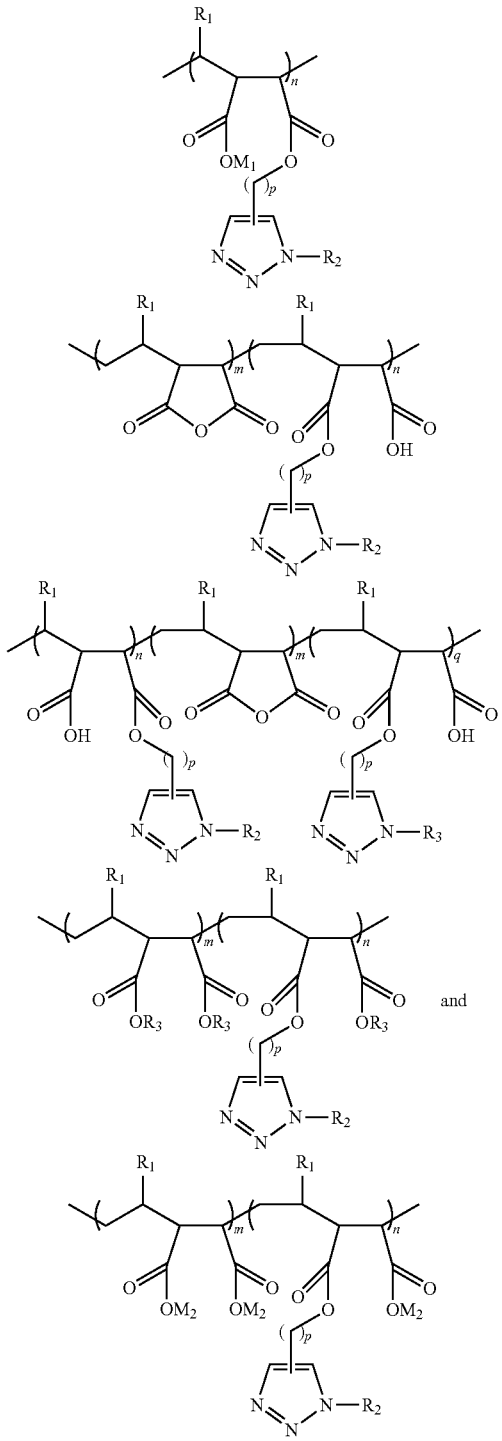

wherein $R_1$, $R_2$; and $R_3$ are each independently selected from the group consisting of hydrogen, functionalized and unfunctionalized alkyl, alkoxy, cycloalkyl, alkenyl, and aryl groups, wherein any of the before mentioned groups may be with or without heteroatoms, and mixtures thereof; $M_1$ is selected from the group consisting of hydrogen, alkali metals, and alkaline earth metals; $M_2$ is an alkali metal or an alkaline earth metal; each m, n, and q is an integer independently ranging from about 2 to about 500; and each p is an integer independently ranging from 1 to about 50.

5. The composition according to claim 4, wherein $R_1$, $R_2$, and $R_3$ are each independently selected from the group consisting of hydrogen and functionalized and unfunctionalized alkyl, alkoxy groups, wherein any of the before mentioned groups may be with or without heteroatoms, and mixtures thereof; X is OH; and each p is an integer independently ranging from 1 to about 50.

6. The composition according to claim 4, wherein the modified polymer is represented by the structure

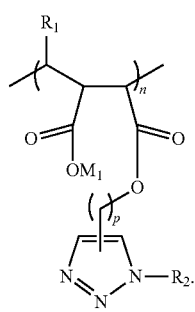

7. The composition according to claim 4, wherein the modified polymer is represented by the structure

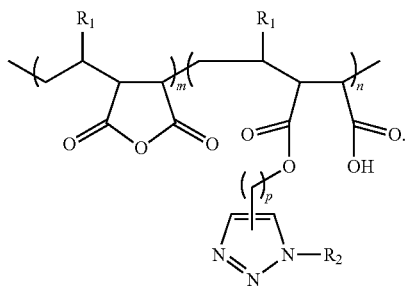

8. The composition according to claim 4 wherein the modified polymer is represented by the structure

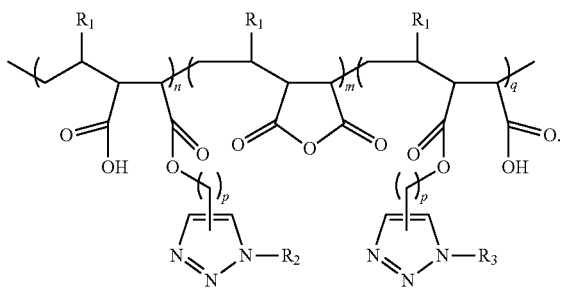

9. The composition according to claim 4, wherein the modified polymer is represented by the structure

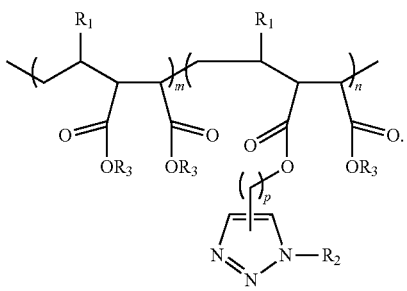

10. The composition according to claim 4, wherein the modified polymer is represented by the structure

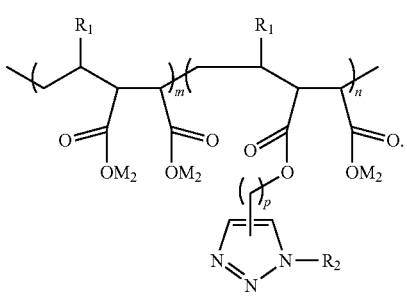

11. A composition comprising a 4 or 5-substituted 1,2,3-triazole, or regioisomer mixtures thereof, modified polymer, wherein the substituted 1,2,3-triazole is modified by a modifying polymer represented by the structure:

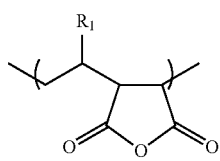

wherein $R_1$ is selected from the group consisting of hydrogen, functionalized and unfunctionalized alkyl, alkoxy, cycloalkyl, alkenyl, and aryl groups, wherein any of the before mentioned groups may be with or without heteroatoms, and mixtures thereof, wherein the composition is selected from the group consisting of cosmetic compositions, drug delivery system compositions, hair compositions, oil compositions, pharmaceutical compositions, pigment dispersion compositions, preservative compositions, color compositions, skin care compositions, sun care compositions, tissue regeneration scaffold compositions, modified natural oil for increased flexibility in styling compositions, durable styling compositions, increased humidity compositions resistance for hair compositions, color compositions, cosmetic compositions, sun care water-proof/resistance compositions, wear-resistance compositions, shower gel compositions, shampoo compositions, thermal protecting/enhancing compositions, denture adhesive compositions, toothpaste compositions, mouth wash compositions, tablet coating compositions, tablet binder compositions, transdermal patch compositions, and mixtures thereof.

* * * * *